US009598714B2

(12) United States Patent
Quaedflieg et al.

(10) Patent No.: US 9,598,714 B2
(45) Date of Patent: Mar. 21, 2017

(54) SIDE-CHAIN PROTECTED OLIGOPEPTIDE FRAGMENT CONDENSATION USING SUBTILISINS IN ORGANIC SOLVENTS

(71) Applicants: Peter Jan Leonard Mario Quaedflieg, Geleen (NL); Timo Nuijens, Geleen (NL)

(72) Inventors: Peter Jan Leonard Mario Quaedflieg, Geleen (NL); Timo Nuijens, Geleen (NL)

(73) Assignee: ENZYPEP B.V., Geleen (NL)

( * ) Notice: Subject to any disclaimer, the term of this patent is extended or adjusted under 35 U.S.C. 154(b) by 226 days.

(21) Appl. No.: 14/379,789

(22) PCT Filed: Feb. 28, 2013

(86) PCT No.: PCT/NL2013/050125
§ 371 (c)(1),
(2) Date: Aug. 20, 2014

(87) PCT Pub. No.: WO2013/129926
PCT Pub. Date: Sep. 6, 2013

(65) Prior Publication Data
US 2015/0037840 A1 Feb. 5, 2015

(30) Foreign Application Priority Data

Feb. 29, 2012 (EP) .................................... 12157571

(51) Int. Cl.
*C12P 21/06* (2006.01)
*C12P 21/00* (2006.01)
*C07K 1/02* (2006.01)
*C07K 1/04* (2006.01)

(52) U.S. Cl.
CPC ............... *C12P 21/00* (2013.01); *C07K 1/02* (2013.01); *C07K 1/026* (2013.01); *C07K 1/04* (2013.01); *C07K 1/042* (2013.01)

(58) Field of Classification Search
CPC . C07K 1/02; C07K 1/026; C07K 1/04; C07K 1/042; C12P 21/00; G06F 21/10; G06F 2221/0724
See application file for complete search history.

(56) References Cited

U.S. PATENT DOCUMENTS 3,479,333 A * 11/1969 Greven ............... C07K 14/695
514/805
2010/0159020 A1* 6/2010 Breitenkamp ....... A61K 9/1075
424/497

FOREIGN PATENT DOCUMENTS

WO  WO 2010/057961 A1 * 5/2010

OTHER PUBLICATIONS

Clapes et al. Peptide 1992, Proc. Eur. Symp. 22md (1993), meeting date 1992; pp. 423-424.*
Guillier et al. Chem. Review (2000) 2091-2157.*
Bjorup, Peter, et al. Reaction Medium Engineering in Enzymatic Peptide Fragment Condensation: Synthesis of Eledoisin and LH-RH, Bioorganic & Medical Chemistry Pergamon, GB, vol. 6, No. 7, Jul. 1, 1998, pp. 891-901, XP027411611.
Nuijens, Timo, et al. Enzymatic synthesis of activated esters and their subsequent use in enzyme-based peptide synthesis, Journal of Molecular Catalysis. B, Enzymatic, Elsevier, Amsterdam, NL, vol. 71, No, 1-2, Aug. 1, 2011, pp. 79-84, XP002664071.
Belyaeva, A.V., et al. Peptide Synthesis in Organic Media with the Use of Subtilisin 72 Immobilized on a Poly (Vinyl Alcohol) Cryogel, Russian Journal of Bioorganic Chemistry, Kluwer Academic Publishers-Plenum Publishers, NE, vol. 31, No. 6, Nov. 1, 2005, pp. 529-534, XP019299983.
Salam, Sayed Mohiuddin Abdus, et al. Alpha-Chymotrypsin-catalyzed peptide synthesis using N-protected-D-amino acid carbamolymethyl esters as acyl donors, Biotechnology Letters, Springer Netherlands, Dordrecht, vol. 27, No. 16, Aug. 1, 2005, pp. 1199-1203, XP019230927.
Wang, Yi-Fong, et al. Cross-Linked Crystals of Subtilisin: Versatile Catalyst for Organic Synthesis, Journal of Organic Chemistry, American Chemical Society, Easton, US, vol. 62, No. 11, May 30, 1997, pp. 3488-3495, XP002107596.

* cited by examiner

*Primary Examiner* — Susan Hanley
(74) *Attorney, Agent, or Firm* — Gianna Julian-Arnold; Saul Ewing LLP

(57) ABSTRACT

Method for enzymatically synthesizing an oligopeptide, comprising the coupling of an (optionally N-protected) protected oligopeptide ester with an (optionally C-protected) protected oligopeptide nucleophile in an organic solvent or an organic solvent mixture having a water content of 0.1 vol % or less, by a subtilisin in any possible form.

17 Claims, 2 Drawing Sheets

SIDE-CHAIN PROTECTED OLIGOPEPTIDE FRAGMENT CONDENSATION USING SUBTILISINS IN ORGANIC SOLVENTS

FIELD OF THE INVENTION

The invention relates to a method for enzymatically synthesizing an oligopeptide.

CROSS-REFERENCE TO RELATED APPLICATIONS

This application claims the priority of PCT/NL2013/050125, filed on Feb. 28, 2013, which claims priority to European Application No. 12157571.6, filed Feb. 29, 2012, the entire contents of each of which are hereby incorporated in total by reference

BACKGROUND OF THE INVENTION

Peptides, in particular oligopeptides have many applications, for instance as pharmaceutical, food or feed ingredient, agrochemical or cosmetic ingredient.

It is known that oligopeptides can be chemically synthesized in solution or on the solid phase via highly optimized processes. However, there are still some limitations in chemical peptide synthesis especially on large scale. For instance, peptides longer than 10-15 amino acids are difficult to synthesize on the solid phase because they tend to form tertiary structures (by so-called "hydrophobic collapse") making peptide elongation very troublesome so that a large excess of reagents and amino acid building blocks is needed. Additionally the purification of the final product is often cost-inefficient due to the presence of significant amounts of peptides of similar length. Therefore, peptides longer than 10 amino acids are often synthesized by a combination of solid phase synthesis of protected oligopeptide fragments which are subsequently chemically condensed in solution, e.g. a 10+10 condensation to make a peptide of 20 amino acids. The major drawback of chemical protected oligopeptide fragment condensation is that upon activation of the C-terminal amino acid residue racemisation occurs, except when C-terminal Gly or Pro residues are used. Therefore, the chemical protected oligopeptide fragment condensation strategy is limited to using C-terminally activated Gly and Pro residues, or one has to deal with a very difficult purification due to the formation of undesired diastereoisomers. In contrast, enzyme-catalyzed oligopeptide couplings are completely devoid of racemisation and have several other advantages over chemical peptide synthesis. For industrial application, an enzymatic peptide synthesis concept based on a kinetic approach, i.e. using an activated carboxy component is most attractive (see for instance Sewald and H.-D. Jakubke, in: "Peptides: Chemistry and Biology", $1^{st}$ reprint, Ed. Wiley-VCH Verlag GmbH, Weinheim 2002).

Chemo-enzymatic peptide synthesis can entail the enzymatic coupling of side-chain unprotected oligopeptide fragments which have individually been synthesized using chemical synthesis, fermentation, or by a combination of chemical and enzymatic coupling steps. Some reports have been published on the enzymatic condensation of fully side-chain unprotected oligopeptides in aqueous environment (Kumaran et al. Protein Science, 2000, 9, 734; Bjorup et al. Bioorg. Med. Chem. 1998, 6, 891; Homandberg et al. Biochemistry, 1981, 21, 3387; Komoriya et al. Int. J. Pep. Prot. Res. 1980, 16, 433). However, a major drawback of such enzymatic oligopeptide fragment condensation in aqueous systems is that simultaneous hydrolysis of the oligopeptide amide bonds and of the C-terminal ester takes place leading to low yields and many side products. To lower the amount of hydrolysis of the expensive oligopeptide starting materials and peptide products, often a large excess of oligopeptide nucleophile is used (5-10 equivalents) to increase the condensation rate and hence decrease the hydrolytic side reactions, which is economically a very unattractive strategy. To further lower the amount of hydrolysis, enzymatic fully unprotected oligopeptide fragment condensations have been performed in low-aqueous reaction mixtures using organic co-solvents showing higher product yields and less hydrolytic side reactions (Slomczynska et al. Biopolymers, 1992, 32, 1461; Xaus et al. Biotechnol. Tech. 1992, 6, 69; Nishino et al. Tet. Lett. 1992, 33, 3137; Clápes et al. Bioorg. Med. Chem. 1995, 3, 245, Kolobanova et al. Russian J. of Bioorg. Chemistry 2000, 26, 6, 369). Because in these reports a significant amount of water is required for enzyme activity (between 1-5 vol % of water), hydrolytic side reactions are still not fully eliminated. To virtually eliminate enzymatic hydrolytic side reactions, near anhydrous reaction mixtures can be used (below 1 vol % water). However there are only very few enzymes active and stable under these conditions (G. Carrea, S. Riva, Fundamentals of Biocatalysis in Neat Organic Solvents, Whiley, 2008) and oligopeptides containing unprotected side-chain functionalities usually display very little or no solubility in these organic solvents. Some reports have been disclosed on the enzymatic synthesis of di- and tri-peptides in anhydrous organic solvents (e.g. Chen et al. J. Org. Chem. 1992, 57, 6960), but no oligopeptide fragment condensations have been performed. Although near anhydrous solvents virtually eliminate hydrolytic side reactions, most often much enzyme activity is lost and thus oligopeptide coupling reactions tend to be very slow and incomplete.

As is known from solution phase chemical peptide synthesis, protected oligopeptides are well soluble in several neat organic solvents due to their hydrophobic character. Thus, enzymatic oligopeptide fragment condensation in anhydrous organic solvents might be performed using protected oligopeptides. However, one would expect that multiple sterically demanding hydrophobic side-chain protecting groups block enzyme recognition. For instance, it was reported by Yan et al. Tetrahedron, 2005, 61, 5933 that no condensation products were obtained at all with side-chain protected amino acids using the protease subtilisin A. According to their observations subtilisin A does not except amino acid residues bearing bulky protecting groups on their side chain functionality; however, when these bulky protecting groups are removed, the amino acid residues are readily accepted.

Gill et al (J. Am. Chem. Soc 1995, 117, 6175-6181) also describe a method for the enzymatic synthesis of oligopeptides. However, the synthesis as described by Gill et al requires specific enzymes for every individual addition of amino acids to synthesize fragments, and another enzyme again for the coupling of two fragments. The fact that different enzymes have to be used for the assembly of the two fragments and another enzyme for the condensation of the two fragments, makes the application of this process on an industrial scale unattractive. Moreover, the fragment condensation step as described by Gill et al requires the removal of two side chain allyl protecting groups of one of the fragments, to allow the use of V8 protease to achieve the coupling. Thus, the process as described by Gill et al is not a versatile process for the preparation of oligopeptides comprising 8 amino acid residues or more.

BRIEF SUMMARY OF THE INVENTION

Thus, there is still a need for a simple versatile enzymatic process for the synthesis of peptides comprising at least 8 amino acid residues, with no or little hydrolytic side reactions. Such an enzymatic process has now surprisingly been found.

DETAILED DESCRIPTION OF THE INVENTION

Figure 1:
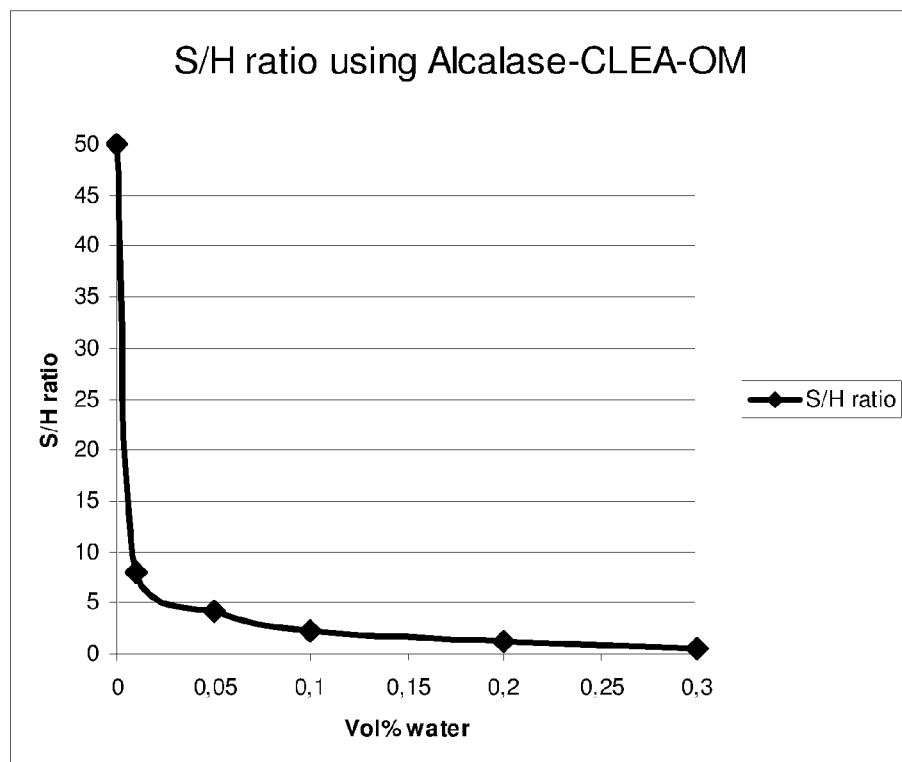
FIG. 1 illustrates the effect of water content on the synthesis/hydrolysis (S/H) ratio of Alcalase-CLEA-OM.

In the framework of this invention, an oligopeptide ester i) is defined as an oligopeptide ester comprising 4 or more amino acid residues,
comprising at least two amino acid residues each with a side-chain functionality that is protected with a protecting group, and comprising an activated C-terminal ester represented by the formula C(=O)—O—CX$_2$—C(=O)N—R$_1$R$_2$, wherein each X independently represents a hydrogen atom or an alkyl group or an aryl group and R$_1$ represents a hydrogen atom or an alkyl group or an aryl group and R$_2$ represents a hydrogen atom or an alkyl group or an aryl group or an amino acid or a peptide residue with a C-terminal carboxyamide or carboxylic acid functionality, optionally protected on the side-chain functionality of the amino acid residue or on one or more of the side-chain functionalities of the peptide residue,
and wherein the oligopeptide ester optionally comprises N-terminal protection.

An oligopeptide nucleophile ii) as used in the process of the present invention is defined as an oligopeptide nucleophile comprising 4 or more amino acid residues,
comprising an N-terminal amine group, and at least two amino acid residues each with a side-chain functionality that is protected with a protecting group and wherein the oligopeptide nucleophile optionally comprises C-terminal protection.

The process of the invention is a process for the enzymatic synthesis of an oligopeptide, comprising coupling an oligopeptide ester i) of 4 or more amino acid residues as defined above, with an oligopeptide nucleophile ii) comprising 4 or more amino acid residues as defined above, which coupling is carried out in an organic solvent or an organic solvent mixture comprising 0.1 vol % or less water relative to the total amount of liquids in which the coupling reaction predominantly takes place, in the presence of a subtilisin and wherein water that is released by the enzyme during the coupling reaction is removed.

For the purpose of this invention, the percentage of water in the solvent mixture is the percentage of water as determined by a Karl Fischer titration carried out exactly as described in the Experimental section.

The oligopeptide ester as described above under i) may in this text also be referred to as "the acyl donor", while the oligopeptide nucleophile ii) is often referred to as "the nucleophile".

With the method of the invention it has been found possible to enzymatically condense protected oligopeptide fragments. In particular, it has surprisingly been found that oligopeptide acyl donors (i.c. the oligopeptide ester as described above) with multiple side-chain protecting groups are accepted as substrate by the enzyme. Furthermore, protected oligopeptide condensation occurs without noticeable side reactions. With the process according to the invention, a yield of more than 80% may be achieved, whereby the percentage is calculated as the amount of acyl donor in mole that has been converted to the desired product, divided by the sum of the remaining acyl donor, desired product and hydrolysis product in mole multiplied by 100%. Preferably, a yield of more than 90%, most preferably a yield of more than 95% is achieved.

Surprisingly, a yield of more than 80% may be achieved, even when using a very small or no excess of one of the coupling partners i) or ii). This is in contrast to enzymatic peptide synthesis in aqueous or low aqueous solutions where a very large excess of the nucleophile is needed to obtain yields of more than 80%, typically 5-10 equivalents.

The method of the invention is advantageous in that it offers the possibility for the coupling of various protected oligopeptides differing in the terminal amino acid residue that is to participate in the coupling reaction, including non-proteinogenic amino acids. No matter which proteinogenic or non-proteinogenic amino acid is used at the C-terminal residue of the C-terminal ester, no racemisation takes place of this residue, whereas in the case of chemical protected fragment condensation always racemisation occurs except if Gly or Pro is used at this position, thus, the method according to the invention offers significantly more freedom in the fragment condensation strategy.

Furthermore, the method of the invention is advantageous in that the extent of hydrolysis of the ester moiety of the protected oligopeptide C-terminal ester is small, i.e. it is small within the typical time frame for achieving the coupling, at least in several experiments no detectable hydrolysis of the ester has been observed. For the purpose of this invention, "small" is defined as less than 5% of the acyl donor, but typically far less than 5% of the acyl donor is hydrolyzed during the method according to the invention. Also the extent of hydrolysis of the amide bonds of the protected oligopeptide fragments or of the enzymatically prepared peptide product is low; at least in several experiments no detectable hydrolysis has been observed.

For the purpose of this invention, with 'oligopeptides' is meant a peptide based on 2-200 amino acids, in particular based on 2-100, more in particular based on 2-50 amino acids, preferably any linear chain of 2-200 amino acids, more preferably of 2-100 or 2-50 amino acids, which is to be used in the method according to the invention. For the purpose of this invention, with "peptides" is meant any chain of amino acids based on 8 or more amino acids, which peptide is the product of a method according to the invention.

For the purpose of this invention, with "protected oligopeptides" is meant any oligopeptide comprising a chain of at least 4 amino acid residues wherein at least two amino acid residues have a side chain functionality and wherein at least two amino acid side-chain functionalities each are protected with a protecting group. Side chain functionalities are for example hydroxyl, carboxylic acid, primary or secondary amine (including indole and guanidino), thiol or carboxyamide functionalities. Preferably, over 60%, more preferably over 70%, and even more preferably over 80% of all side chain functionalities that are present are protected.

For the purpose of this invention, with "unprotected oligopeptides" is meant any oligopeptide having less than two amino acid residues of which the side chain functionality is protected.

In the context of the invention with 'amino acid side chain' is meant any proteinogenic or non-proteinogenic amino acid side chain.

Proteinogenic amino acids are the amino acids that are encoded by the genetic code. Proteinogenic amino acids include: alanine (Ala), valine (Val), leucine (Leu), isoleucine (Ile), serine (Ser), threonine (Thr), methionine (Met), cysteine (Cys), asparagine (Asn), glutamine (Gln), tyrosine (Tyr), tryptophan (Trp), glycine (Gly), aspartic acid (Asp), glutamic acid (Glu), histidine (His), lysine (Lys), arginine (Arg), proline (Pro) and phenylalanine (Phe).

Non-proteinogenic amino acids may in particular be selected amongst D-amino acids, phenylglycine, DOPA (3,4-dihydroxy-L-phenylalanine), beta-amino acids, 4-fluoro-phenylalanine, or $C^\alpha$-alkylated amino acids.

For the purpose of this invention, with condensation is meant the formation of a new peptide bond between two oligopeptides.

In the framework of this invention, with amino acid residue or peptide residue is meant an amino acid or a peptide, minus the N-terminal amino group of that amino acid or peptide.

The term 'C-terminal protection' is used herein to indicate that a C-terminal carboxylic function is provided with a protective group, generally substantially protecting the carboxyl group from being coupled to an amine group of another molecule. The C-terminal protective group may be a C-terminal ester whereby the C-terminal carboxyl group is at least substantially protected from being coupled to an amine under peptide synthesis conditions used. A t-alkyl group is a commonly used protective group. The C-terminal protective group may also be a C-terminal carboxyamide. A primary carboxy amide is a commonly used protective group. The C-terminal protective group may also be a hydrazide, a carbamoyl-hydrazide or a thioester. The C-terminal protection may be temporary or permanent, the latter meaning that this protective moiety is part of the desired end product.

The term 'N-terminal protection' is used herein to indicate that an N-terminal amine group is provided with a protective group, generally at least substantially protecting the N-terminal amine group from participating in coupling of a C-terminal carboxyl group to the N-terminal amine group.

The ester —C(=O)O—CX$_2$—C(=O)N—R$_1$R$_2$ moiety in the protected oligopeptide C-terminal ester i) used in the enzymatic condensation of protected oligopeptides is an activated ester. An activated ester is an ester which provides a carboxy ester group that can take part in the coupling reaction.

Herein, each X independently represents a hydrogen atom or an alkyl group or an aryl group. Particularly good results have been achieved in a method of the invention wherein each X is a hydrogen (—O—CH$_2$—C(=O)N—, referred to as Cam-ester).

In said ester moiety, R$_1$ represents a hydrogen atom or an alkyl group or an aryl group and R$_2$ represents a hydrogen atom or an alkyl group or an aryl group or an amino acid or a peptide residue with a C-terminal carboxyamide or carboxylic acid functionality, optionally protected on the side-chain functionality of the amino acid residue or on one or more of the side-chain functionalities of the peptide residue.

In this text, wherever the word "alkyl group" or "aryl group" is used, the following definitions apply: each alkyl group may independently represent a (substituted or unsubstituted) C1-C7 alkyl group, preferably a (substituted or unsubstituted) linear C1-C6 alkyl group, more preferably a (substituted or unsubstituted) linear C1-C3 alkyl group, and most preferably a methyl group.

Each aryl group may independently represent a (substituted or unsubstituted) C4-C13 aryl group, preferably a (substituted or unsubstituted) C4-C6 aryl group, more preferably a (substituted or unsubstituted) C6 aryl group, and most preferably a phenyl group. The aryl group may optionally comprise one or more heteroatoms in a ring thereof. A heteroatom may in particular be selected from the group of S, O and N. Substituents on the alkyl or aryl group may be any atom or group of atoms that does not prevent the coupling reaction between the oligopeptide ester i) and the oligopeptide nucleophile ii) from taking place. A person skilled in the art can easily test which substituents are usable in the method according to the invention and which are not.

Good results have in particular been achieved in a method of the invention wherein both R$_1$ and R$_2$ represent a hydrogen atom or wherein R$_1$ represents a hydrogen atom and R$_2$ represents an amino acid or peptide residue with a C-terminal carboxyamide or carboxylic acid functionality, optionally protected on the side-chain functionality of the amino acid residue or on one or more of the side-chain functionalities of the peptide residue.

In another embodiment, the activated C-terminal ester group of the protected oligopeptide ester can be introduced on the solid phase in high yields and high purity without racemisation. An additional advantage of the use of esters wherein R$_1$ represents a hydrogen atom and R$_2$ represents an amino acid or peptide residue with a C-terminal carboxylic acid functionality, optionally protected on the side-chain functionality of the amino acid residue or on one or more of the side-chain functionalities of the peptide residue, that their activated C-terminal ester group can be introduced on the cheap and industrially available 2-chlorotrityl resin.

The C-terminal amino acid of the protected oligopeptide ester i) may in principle be any amino acid, proteinogenic or non-proteinogenic and the oligopeptide ester may consist of proteinogenic and/or non-proteinogenic amino acids.

In particular the (optionally N-terminal protected) activated ester i) may be represented by a compound of formula I.

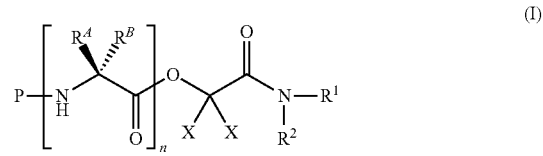

Herein P stands for a hydrogen or N-terminal protecting group. Suitable N-terminal protecting groups are those N-protecting groups which can be used for the synthesis of (oligo)peptides. Such groups are known to the person skilled in the art. Examples of suitable N-protecting groups include carbamate or acyl type protecting groups, for instance 'Cbz'

(benzyloxycarbonyl), 'Boc' (tert-butyloxycarbonyl), 'For' (formyl), 'Fmoc' (9-fluorenylmethoxycarbonyl), 'PhAc' (phenacetyl) and 'Ac' (acetyl). The groups For, PhAc and Ac may be introduced and cleaved enzymatically using the enzymes Peptide Deformylase, PenG acylase or Acylase, respectively. Chemical cleavage methods are generally known in the art.

In formula I, n represents an integer of at least 4. n May in particular be at least 5, at least 6, at least 7, at least 8, at least 9 or at least 10. n May in particular be 100 or less, 75 or less, 50 or less, 25 or less, 20 or less 15 or less, e.g. 10 or less.

In formula I, each $R^A$ and each $R^B$ independently represent a hydrogen atom or an organic moiety, preferably an amino acid side chain. Thus, it is not required that $R^A$ is the same in all n amino acid units. Similarly, it is not required that $R^B$ is the same in all n amino acid units. At least two amino acid residues in the oligopeptide ester according to formula I each comprise a side chain with a protecting group, i.e for each of those amino acid residues $R^A$ or $R^B$ is not H and each has a protected functional group, e.g. a protected hydroxyl, carboxylic acid, primary or secondary amine (including e.g. indole and guanidino), thiol or primary amide functionalities i.e. have a protected side-chain functionality. Preferably, at least 50% percent of the functional groups present in $R^A$ and $R^B$ taken together should be protected with protecting groups known in the art. Many different protecting groups are known, and can be used in the method according to the invention. If Fmoc based solid-phase peptide synthesis is used, the side-chain protecting groups can for instance be selected from the t-Bu (tert-butyl), Boc, Trt (trityl), Mtt (4-methyltrityl), Acm (acet-amidomethyl), Dnp (2,4-dinitrophenyl), Pmc (2,2,5,7,8-pentamethylchroman-6-sulfonyl) or Pbf (2,2,4,6,7-pentamethyldihydrobenzofuran-5-sulfonyl) groups. If Boc based solid-phase peptide synthesisis is used, the side-chain protecting groups can for instance be selected from the Bzl (benzyl), Bz (benzoyl), 2Cl—Z (2-chlorobenzyloxycarbonyl), cHex (cyclohexyl), Tos (tosyl), Xan (xanthenyl), For or Mbzl (4-methoxybenzyl) and 3-benzyloxymethyl groups.

In a preferred embodiment, all side-chain functionalities of the oligopeptide ester i) are protected except for the side-chain functionality of the C-terminal amino acid residue of the oligopeptide acyl-donor, i.e. the activated C-terminal ester. The advantage of this embodiment is that higher yields and/or shorter reaction times can be achieved than in embodiments wherein the side-chain functionality of the C-terminal amino acid residue of the oligopeptide acyl donor i) is protected.

The (optionally C-terminal protected) protected oligopeptide nucleophile ii) that is to be coupled with the activated ester i) may in principle be any peptide based on proteinogenic or non-proteinogenic amino acids.

In particular, the (optionally C-terminal protected) protected oligopeptide nucleophile ii) may be represented by a compound of formula II:

Herein, n, $R^A$ and $R^B$ are as defined above. At least two amino acid residues in the oligopeptide nucleophile according to formula II each comprise a side chain with a protecting group, i.e for each of those amino acid residues $R^A$ or $R^B$ is not H and each has a protected functional group, e.g. a protected hydroxyl, carboxylic acid, primary or secondary amine (including e.g. indole and guanidino), thiol or primary amide functionalities i.e. have a protected side-chain functionality. Preferably, at least 50% percent of the functional groups present in $R^A$ and $R^B$ taken together should be protected with protecting groups known in the art.

Herein Q represents an OR moiety, an amine group, a hydrazine group, a carbamoyl-hydrazine group or an SR moiety.

In case Q represents an OR moiety, R may represent a C-terminal protective group, a hydrogen atom or a cation, for instance a monovalent cation, such as a tri- or tetrasubstituted ammonium ion or an alkaline metal cation. In case R is a C-terminal protective group this may in particular be an (optionally substituted) alkyl group or an (optionally substituted) aryl group. In case R is a C-terminal protective group, R is preferably a t-alkyl group, although in principle it also may be any other protective group as known to a man skilled in the art. The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl).

In case Q represents an amine group, the amine group may be represented by the formula $NR_3R_4$, in which $R_3$ and $R_4$ may each individually represent a hydrogen atom, any (substituted or unsubstituted) alkyl or any (substituted or unsubstituted) aryl group. In particular, one out of $R_3$ and $R_4$ may be a hydrogen atom and the other a (substituted or unsubstituted) alkyl group. Good results have particularly been obtained with $R_3$ and $R_4$ both being a hydrogen atom.

In case Q represents a hydrazine group, the hydrazine group may be represented by the formula $NR_5$—$NR_6R_7$, in which $R_5$, $R_6$ and $R_7$ may each individually represent a hydrogen atom, any (substituted or unsubstituted) alkyl or any (substituted or unsubstituted) aryl group. Preferably, $R_5$, $R_6$ and $R_7$ are all a hydrogen atom.

In case Q represents a carbamoyl-hydrazine group, the carbamoyl-hydrazine group may be represented by the formula $NR_8$—$NR_9C(O)NR_{10}R_{11}$, in which $R_8$, $R_9$, $R_{10}$ and $R_{11}$ may each individually represent a hydrogen atom, any (substituted or unsubstituted) alkyl or any (substituted or unsubstituted) aryl group. Preferably, $R_8$, $R_9$, $R_{10}$ and $R_{11}$ are all a hydrogen atom.

In case Q represents an SR moiety, R may represent a C-terminal protective group, a hydrogen atom or a cation, for instance a monovalent cation, such as a tri- or tetrasubstituted ammonium ion or an alkaline metal cation. In case R is a C-terminal protective group this may in particular be an (optionally substituted) alkyl group or an (optionally substituted) aryl group. In case R is a C-terminal protective group, R is preferably a t-alkyl group, although in principle it also may be any other protective group as known to a man skilled in the art. The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl).

In the method of the invention the coupling of the protected oligopeptide ester with the protected oligopeptide nucleophile, is catalysed by a subtilisin (E.C. 3.4.21.62). In principle any subtilisin capable of catalyzing the coupling reaction can be used. When referring to a subtilisin from a particular source, recombinant subtilisins originating from a first organism, but actually produced in a (genetically modified) second organism, are specifically meant to be included as enzymes from that first organism.

Preferably, the subtilisin used in the method of the invention is subtilisin A.

Various subtilisins are known in the art, see e.g. U.S. Pat. No. 5,316,935 and the references cited therein. Such subtilisins may be used in the method according to the invention.

The use of Subtilisin A in a process according to the invention wherein a peptide ester i) is used containing a Proline residue on the C-terminal position, usually results in very slow coupling reactions. Therefore, in a preferred embodiment, the method according to the invention is carried out with the proviso that the C-terminal amino acid residue in the oligopeptide ester i) is not a Proline residue if the reaction is carried out in the presence of wild type Subtilisin A. Also for other subtilisins, it is preferred to use an oligopeptide ester i) wherein the C-terminal amino acid residue is not a Proline residue. However, it is to be expected that with mutants of Subtilisin A an acceptable coupling rate can be achieved.

Examples of organisms from which a subtilisin used in the method of the invention may be derived include *Trichoderma* species, such as from *Trichoderma reesei*; *Rhizopus* species, such as from *Rhizopus oryzae*; *Bacillus* species, such as from *Bacillus licheniformis*, *Bacillus subtilis*, *Bacillus amyloliquefaciens*, *Bacillus clausii*, *Bacillus lentus*, *Bacillus alkalophilus*, *Bacillus halodurans*; *Aspergillus* species, such as from *Aspergillus oryzae* or *Aspergillus niger*; *Streptomyces* species, such as from *Streptomyces caespitosus* or *Streptomyces griseus*; *Candida* species; fungi; *Humicola* species; *Rhizoctonia* species; *Cytophagia*; *Mucor* species; and animal tissue, in particular from pancreas, such as from porcine pancreas, bovine pancreas or sheep pancreas.

It will be clear to the average person skilled in the art that use can also be made of mutants of naturally occurring (wild type) subtilisins in a method according to the invention. Mutants of wild-type enzymes can for example be made by modifying the DNA encoding the wild-type enzymes using mutagenesis techniques known to the person skilled in the art (random mutagenesis, site-directed mutagenesis, directed evolution, gene shuffling, etc.) so that the DNA encodes an enzyme that differs by at least one amino acid from the wild-type enzyme or so that it encodes an enzyme that is shorter compared to the wild-type and by effecting the expression of the thus modified DNA in a suitable (host) cell. Mutants of the enzyme may have improved properties, for instance with respect to one or more of the following aspects: substrate scope, activity, stability, organic solvent resistance, temperature profile, synthesis/hydrolysis ratio and side reaction profile.

In a preferred method subtilisin A is used to catalyse the coupling reaction. Subtilisin A is a commercially available subtilisin from Novozymes and has been found particularly advantageous with respect to condensing the protected coupling partners to give the desired peptide product with a good yield in a relatively short time.

Alcalase® is a suitable source for subtilisin A. This product is available from Novozymes (Bagsvaerd, Denmark). Alcalase® is a cheap and industrially available proteolytic enzyme mixture produced by *Bacillus licheniformis* (containing subtilisin A as a major enzyme component).

Commercially available enzymes, such as Alcalase®, may be provided by the supplier as a liquid, in particular an aqueous liquid. In such case, the enzyme is preferably first isolated from undesired liquid, for instance excess water or alcohols that cause an undesired side-reaction. This may suitably be accomplished by precipitating, usually followed by separation of the solid from the liquid, and/or drying. Precipitation may be accomplished using an alcohol, such as t-butanol. In case another alcohol is used, care should be taken that such alcohol does not interfere adversely with the coupling reaction.

In a preferred embodiment, the enzyme is used in an immobilized form. At least in some embodiments this may result in an increased yield of synthesised oligopeptide after a relatively short reaction time. Particularly good results have been obtained with Alcalase cross-linked enzyme aggregates (Alcalase-CLEAs) or with Alcalase immobilized on solid particles such as Alcalase-Imibond, Alcalase-Epobond, Alcalase-immozyme or Alcalase-Decalite. Immobilisation of the enzyme also may allow easy recovery of the enzyme after the coupling reaction, so that it can be recycled and repeatedly used in consecutive coupling reactions.

It is possible to carry out the enzymatic coupling reaction in an inert organic solvent. Some examples of suitable solvents are for instance N,N-dimethylformamide (DMF), N-methyl-pyrrolidinone (NMP), N,N-dimethylacetamide (DMA), dimethylsulphoxide (DMSO), acetonitrile, a hydrocarbon such as toluene, a halogenated hydrocarbon, such as dichloromethane, 1,2-dichloroethane or chloroform, an ether, such as methyl-t-butyl ether (MTBE), tetrahydrofuran (THF), 2-methyl-tetrahydrofuran (Me-THF) or 1,2-dimethoxyethane, or a (halogenated) alcohol, such as 2,2,2-trifluoroethanol (TFE) or a mixture of these organic solvents. Preferably, the enzymatic coupling reaction may be carried out in an organic solvent or organic solvent mixture comprising MTBE, THF, Me-THF, 1,2-dimethoxyethane, dichloromethane, 1,2-dichloroethane, TFE, DMF, NMP, DMA or DMSO. Most preferably, the enzymatic coupling reaction may be carried out in an organic solvent or organic solvent mixture comprising MTBE, a mixture of MTBE with DMF or NMP or DMA or DMSO, dichloromethane or a mixture of dichloromethane with DMF or NMP or DMA or DMSO.

The enzymatic fragment condensation is typically carried out under substantially non-aqueous conditions. As the skilled person will understand, a small amount of water may be desired, depending upon the enzyme, to enable the enzyme to properly perform its catalytic activity.

With substantially non-aqueous is meant that the reaction medium is free of water or contains a minimal amount of water, i.e. an amount of 0.1 vol % or less water, based on the total volume of liquids in the reaction medium. The reaction medium may be dispersed in a second liquid phase or another liquid phase may be dispersed in the reaction medium. In case of a dual or multiphase system, the specified water content is based on the volume of liquids in the phase wherein the coupling reaction takes place, or when a multi-phase system exists, wherein the coupling reaction at least predominantly takes place A desired upper limit for the water concentration depends on the concentrations of oligopeptide ester i) and oligopeptide nucleophile ii), on the specific enzyme, the solvent used, the nature of the peptide to be synthesised (e.g. the size of the peptide and the sequence of the amino acids), the desired final conversion and the desired reaction rate.

In the method according to the invention, the water concentration is 0.1 vol % or less, more preferably 0.05 vol % or less, even more preferably 0.01 vol % or less.

No lower limit for the water concentration is presented here, because the minimal amount of water that may need to be present is below the detection limits of well known analytical methods. This also holds true for the detection limit of the Karl-Fischer titration that is used to determine the water concentration for the method according to the invention. In an advantageous embodiment, water that is released by the enzyme, may be removed continuously or intermittently. In principle, the water removal may be accomplished in a manner known in the art. Very suitable for the water removal is evaporation, such as azeotropic removal using vacuum or distillation. Good results have in particular been achieved using molecular sieves. However, it is important to retain substantially the desired enzyme activity.

The addition of various amounts of molecular sieves to the enzymatic coupling reaction allows the variation of the water concentration below its detection limit. A too low water concentration, for instance obtained by the addition of a large amount of molecular sieves, may in some cases lead to gradual (partial) enzyme deactivation during the coupling reaction. The man skilled in the art can easily determine the optimal water concentration for a certain coupling reaction by variation of the amount of molecular sieves. In case of (partial) enzyme deactivation during the enzymatic coupling reaction, the (partly) deactivated enzyme may be completely or almost completely reactivated by rehydration, for instance by stirring the (partly) deactivated enzyme in an aqueous solution. This reactivation may allow repeated use of the enzyme in consecutive coupling reactions. In some cases, in particular with lyophilized enzymes, the enzyme needs to be hydrated before the enzymatic coupling in order to get sufficient catalytic activity. In case of non-immobilized enzymes such a hydration may be performed by stirring in aqueous solution followed by precipitation, for instance with a water-miscible organic solvent such as t-butanol. In case of immobilized enzymes such a hydration may be performed by washing with an aqueous solution, followed by washing with one or more organic solvents, for instance with a water-miscible organic solvent such as t-butanol and a water-immiscible solvent such as MTBE.

In particular, the method of the invention allows coupling of an oligopeptide ester i) to an oligopeptide nucleophile ii), without needing a large excess of one of the coupling partners based on the other coupling partner in order to obtain the synthesised peptide in an acceptable yield within a relatively short time. The molar ratio of the oligopeptide ester i) to the oligopeptide nucleophile ii) usually is chosen in the range of 2:1 to 1:4, in particular in the range of 1:1 to 1:3, preferably in the range of 1:1 to 1:2, more preferably 1:1 to 1:1.5, even more preferably 1:1 to 1:1.2.

In a preferred embodiment, the coupling reaction is performed in the absence of a salt. Such a salt is usually formed by the addition of a base to neutralise the salt of the (optionally C-terminal protected) protected oligopeptide nucleophile ii) which is formed after the acidic cleavage of the protected oligopeptide from the solid phase using for instance 1-2.5 vol % trifluoroacetic acid in dichloromethane. The presence of a salt in the (optionally C-protected) protected oligopeptide amine nucleophile ii) can conveniently be avoided by aqueous alkaline extraction of the dichloromethane layer after cleavage of the protected oligopeptide from the solid phase.

In principle the pH used (in as far as a pH exists in the chosen reaction medium) may be chosen within wide limits, as long as a pH is chosen at which the enzyme shows sufficient activity. Such a pH is usually known for the enzyme to be used and may be based on its known hydrolytic activity in an aqueous solution, or can be routinely determined, making use of a known substrate for the enzyme under known reaction conditions. It may in particular be chosen to be about neutral. If desired, alkaline or acidic conditions may be used, depending on the enzyme. If desired, the pH may be adjusted using an acid and/or a base or the pH may be buffered with a suitable combination of an acid and a base. Suitable acids and bases are in particular those soluble in the reaction medium, e.g. from the group of ammonia and organic solvent-soluble acids, such as acetic acid and formic acid.

In principle the temperature used is not critical, as long as a temperature is chosen at which the enzyme(s) used show sufficient activity and stability. Such a temperature is usually known for the enzyme(s) to be used or can be routinely determined, making use of a known substrate for the enzyme(s) under known reaction conditions. Generally, the temperature may be at least 0° C., in particular at least 15° C. or at least 25° C. In particular if one or more enzyme(s) originating from a thermophilic organism are used, the temperature may preferably be at least 35° C. A desired maximum temperature depends upon the enzyme(s). In general such maximum temperature is known in the art, e.g. indicated in a product data sheet in case of commercially available enzyme(s), or can be determined routinely based on common general knowledge. The temperature is usually 70° C. or less, in particular 60° C. or less or 50° C. or less. However, in particular if one or more enzyme(s) from a thermophilic organism are used, the temperature may be chosen higher, for example up to 90° C.

Optimal temperature conditions can easily be identified for a specific enzyme by a person skilled in the art through routine experimentation based on common general knowledge. For instance, for subtilisin, in particular subtilisin A (e.g. in Alcalase®), the temperature may advantageously be in the range of 25–60° C. The oligopeptide ester i) and the oligopeptide nucleophile ii) to be coupled in the process according to the invention are preferably synthesized through a solid-phase synthesis approach.

Peptide C-terminal carbamoylmethyl (Cam) and Cam-Xxx-$NH_2$ esters (wherein Xxx represents any side-chain protected or unprotected proteinogenic or non-proteinogenic amino acid) have been earlier applied in protease catalyzed peptide synthesis (see for instance Miyazawa et al. Protein & Peptide Letters, 2008, 15, 1050) and are usually more rapidly enzymatically condensed than alkyl esters but also much more prone to hydrolysis.

Solid phase synthesis techniques have been described for the synthesis of fully side-chain unprotected oligopeptide C-terminal Cam-esters (see for instance Bjorup et al. Bioorg. Med. Chem., 1998, 6, 891). These peptide C-terminal Cam-esters are synthesized on the solid phase containing a Rink or Pal linker (See *Schematic representation* 1, H. Rink, Tetrahedron letters, 1987, 28, 3787; F. Albericio et al. J. Org. Chem., 1990, 55, 3730) and cleaved with simultaneous side-chain deprotection using high concentrations of TFA (e.g. TFA/$H_2O$, 95/5, v/v). Unfortunately these harsh cleavage and side-chain deprotection conditions also lead to undesired partial hydrolysis of the Cam-ester.

Schematic representation 1.

Solid phase synthesis of side-chain unprotected peptide C-terminal Cam-esters

▓ = protecting group

■ = peptide fragment

Rink linker

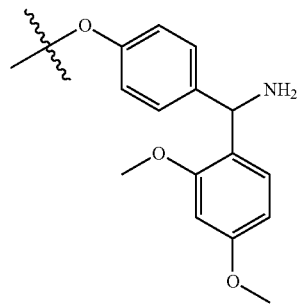

Solid phase with Pal or Rink linker

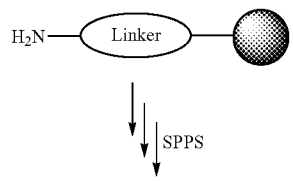

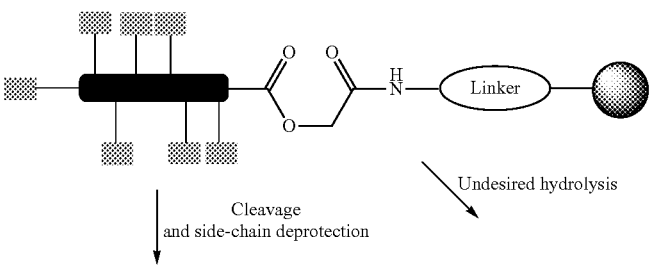

Cleavage and side-chain deprotection

Undesired hydrolysis

Pal linker

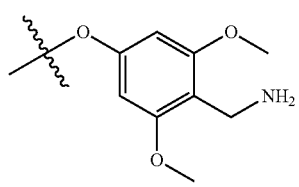

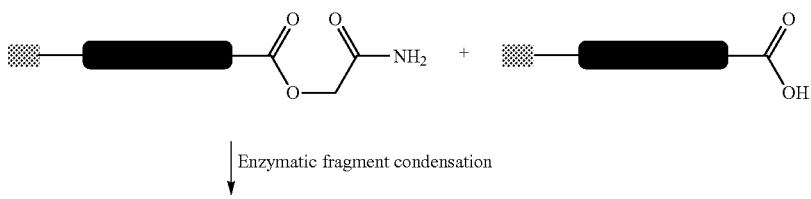

Enzymatic fragment condensation

Inventors have now found, however, that it is possible to synthesize side-chain protected peptide C-terminal Cam and Cam-Xxx-NH$_2$ esters on the solid phase. A special Sieber or Ramage amide linker (See *Schematic representation 2*, Sieber, *Tetrahedron letters*, 1987, 28, 2107; Ramage et al. *Tetrahedron letters*, 1993, 34, 6599) is used and the peptides are cleaved under very mild acidic conditions (e.g. 2.5 vol % TFA in CH$_2$Cl$_2$) leaving the side-chain protecting groups unaffected. These types of linkers have hitherto never been used for the synthesis of peptide C-terminal Cam-esters.

Schematic representation 2:

Solid phase synthesis of side-chain unprotected peptide C-terminal Cam-esters

▓ = protecting group

■ = peptide fragment

Sieber linker

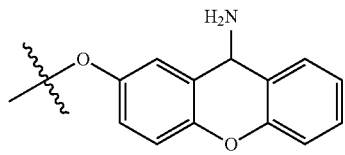

Ramage linker

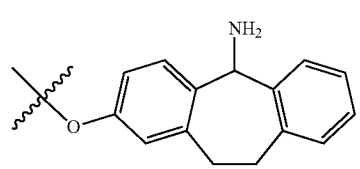

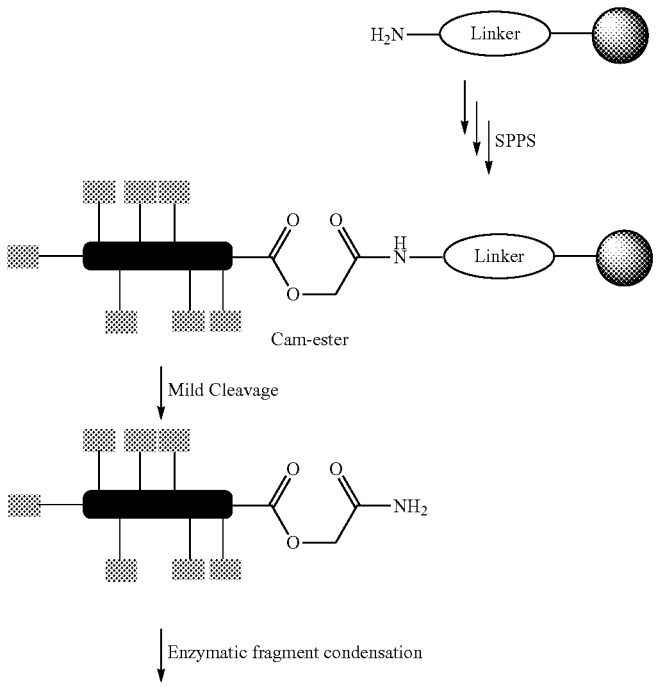

Advantageously, the cleavage of the side-chain protected peptide C-terminal Cam-esters from the solid phase is not accompanied by any undesired hydrolysis of the Cam-ester. Besides the Cam-ester synthesis on a resin with a Sieber or Ramage linker, inventors have now found that it is possible to synthesize side-chain protected peptide C-terminal Cam-Xxx-OH esters (wherein Xxx represents any side-chain protected or unprotected proteinogenic or non-proteinogenic amino acid) on the solid phase containing a 2-chlorotritylchloride or SASRIN linker (See Schematic representation 3, Barlos, Tetrahedron Letters, 1973, 95, 1328; Mergler et al. Tetrahedron Letters, 1988, 68, 239). Surprisingly, these Cam-Xxx-OH esters performed equally well in the enzymatic fragment condensation reactions as the Cam-Xxx-NH$_2$ esters.

Schematic representation 3:

2-chlorotritylchloride and SASRIN linker

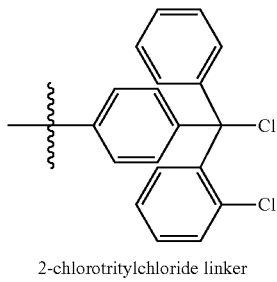

2-chlorotritylchloride linker

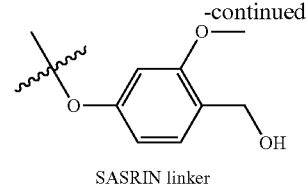

SASRIN linker

In the literature it has been proven advantageous to combine solid-phase chemical peptide synthesis techniques with enzymatic fragment condensations. However, these examples were based on the solid phase synthesis of fully side-chain unprotected peptides and the subsequent enzymatic condensation of these peptide fragments in aqueous or partially aqueous solution (see for instance Čerovský et al. J Pept Res., 2000, 55, 325).

On the contrary, in a preferred method of the invention side-chain protected peptide fragments are synthesized via solid phase techniques and subsequently enzymatically condensed in an anhydrous organic solvent, which has never been disclosed before.

Thus, the invention also relates to a process for the synthesis of an oligopeptide ester i) comprising an ester moiety represented by the formula C(=O)—O—CX$_2$—C(=O)N—R$_1$R$_2$ (i.e. a Cam-ester) as described above.

The invention also relates to a process for the synthesis of a peptide, by
a) preparing an oligopeptide ester i) as defined before by solid phase synthesis using a linker between the solid phase and the oligopeptide that is suitable to allow cleavage of the oligopeptide ester from the solid phase with retention of any side chain protecting groups present on the oligopeptide, under mild acidic conditions, and wherein the oligopeptide ester is cleaved from the solid phase, b) preparing an oligopeptide nucleophile ii) as defined before, by solid phase synthesis using a linker between the solid phase and the oligopeptide that is suitable to allow cleavage of the oligopeptide nucleophile from the solid phase with retention of any side chain protecting groups present on the oligopeptide, under mild acidic conditions, and wherein the oligopeptide nucleophile is cleaved from the solid phase, and c) subsequently coupling of the oligopeptide ester i) with the oligopeptide nucleophile ii) which coupling is carried out in an organic solvent or an organic solvent mixture comprising 0.1 vol % or less water relative to the total amount of liquids in which the coupling reaction predominantly takes place in the presence of a subtilisin and wherein water that is released by the enzyme during the coupling reaction is removed.

Surprisingly, the enzymatic fragment condensation strategy is compatible with the most commonly applied Fmoc-based solid phase peptide synthesis side chain protecting groups. Even peptides containing large "bulky" side-chain protecting groups such as Trt, Pbf or Pmc are recognized by the enzyme and condensed in good to excellent yield. These types of protecting groups have until now never been applied in enzymatic peptide synthesis. The most commonly used side-chain protection groups for Fmoc/$^t$Bu based solid phase peptide synthesis are:

$^t$Bu for Asp, Glu, Thr, Ser and Tyr, Boc for Lys and Trp, Trt for His, Asn, Gln and Cys and Pmc or Pbf for Arg.

The most commonly used side-chain protection groups for Boc/Bzl based solid phase peptide synthesis are:

Tos or Mts for Arg, Bzl or Cy for Asp, Glu, Thr and Ser, Acm for Cys, Bom or Dnp for His 2-Cl-Cbz for Lys, For for Trp and 2-Br-Cbz for Tyr.

The invention will now be illustrated by the following examples without being limited thereto.

EXPERIMENTAL

Unless stated otherwise, chemicals were obtained from commercial sources and used without further purification. The Sieber (or Xanthenyl linker) resin and 2-chlorotrityl resin were purchased from GL Biochen (China). Savinase, Esperase and Everlase were purchased from Novozymes. Protease from Bacillus sp. (three different variants) and Protease from Bacillus licheniformis were purchased from Sigma. Alcalase-immozyme was purchased form ChiralVision. 1H and 13C NMR spectra were recorded on a Bruker Avance 300 MHz NMR spectrometer and chemical shifts are given in ppm (δ) relative to TMS (0.00 ppm), DMSO-d6 (2.50 ppm for 1H or 39.9 ppm for 13C) or CDCl$_3$ (77.0 ppm for 13C). Thin layer chromatography (TLC) was performed on pre-coated silica gel 60 F254 plates (Merck); spots were visualized using UV light or ninhydrin. 3 Å molecular sieves (8 to 12 mesh, Acros) were activated under reduced pressure at 200° C. Tert-butanol (tBuOH) was stored on these molecular sieves. tBuOH was pre-heated to a liquid (45° C.) before use. Column chromatography was carried out using silica gel, Merck grade 9385 60 Å. Analytical HPLC was performed on an HP1090 Liquid Chromatograph, using a reversed-phase column (lnertsil ODS-3, C18, 5 μm, 150×4.6 mm) at 40° C. UV detection was performed at 220 nm using a UV-VIS 204 Linear spectrometer. The gradient program was: 0-25 min linear gradient ramp from 5% to 98% eluent B and from 25.1-30 min with 5% eluent B (eluent A: 0.5 mL/L methane sulfonic acid (MSA) in H$_2$O, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 20 μL. Analysis of large protected hydrophobic peptides (>10 amino acids) was performed using the following gradient program: 0-60 min linear gradient ramp from 0% to 100% eluent B and from 60-65 min with 100% eluent B (eluent A: 1 mL/L TFA in water/acetonitrile (80/20 v/v %), eluent B 1 mL/L TFA in acetonitrile/2-propanol/water (50/45/5, v/v/v %)). LC-MS analysis was performed using the same buffers and gradient programs as for analytical HPLC. Chromatograms were recorded on a Deca XP ion trap LC-MS (ThermoFisher Scientific) using a positive ion electro spray (ESI) in full scan mode: range of 300-2000 amu. The product yields of the condensation reactions were determined by comparing the integrated areas of the product peak with those of the starting materials and assuming that the extinction coefficient of the product is equal to that of the acyl donor. Preparative HPLC was performed on a Varian PrepStar system using a stationary-phase column (Pursuit XRs, C18, 10 μm particle size, 500×41.4 mm). Alcalase-CLEA-OM was purchased from CLEA-Technologies and contained 3.5 wt % water; the apparent activity was 650 AGE units per gram (with 1 AGE unit catalyzing the formation of 1 μmol N-acetyl-glycine from N-acetyl-glycine ethyl ester at 40° C. and pH 7.5). This Alcalase-CLEA-OM was treated as follows before use: 1 g Alcalase-CLEA-OM was suspended in 20 mL $^t$BuOH and crushed with a spatula. After filtration, this procedure was repeated with 20 mL MTBE. Finally the enzyme was sieved (d=0.250 mm) to remove large enzyme particles. Liquid alcalase was treated as follows before use: 10 mL of Alcalase (brown liquid solution, Novozymes type 2.5 L DX) was diluted with 20 mL $^t$BuOH followed by agitation and subsequent centrifugation of the precipitates (3.500 rpm) and decantation of the supernatant. The pellet was resuspended in 30 mL $^t$BuOH followed by agitation, centrifugation and decantation (3.500 rpm). The resulting pellets were used in the method according to the invention. Alcalase-imibond and Alcalase-epobond were purchased from SPRIN technologies (Trieste, Italy) and washed with phosphate buffer (10 mL/g, 100 mM, pH 7.5, 3×), $^t$BuOH (3×) and MTBE. The same washing procedure was applied for Alcalase-immozyme. Subtilisine A and Proteinase K lyophilised powders (Sigma) were hydrated as follows before use: 1 gram of lyophilised powder was dissolved in 10 mL phosphate buffer (100 mM, pH 7.5) followed by the addition of 20 mL $^t$BuOH followed by agitation and subsequent centrifugation of the precipitates (3.500 rpm) and decantation of the supernatant. The pellet was resuspended in 30 mL $^t$BuOH followed by agitation, centrifugation and decantation (3.500 rpm). This procedure was repeated twice.

Description of the Karl Fischer Titration to be Used to Determine the Percentage of Water in the Reaction Mixture The water content was measured automatically using a Metrohm titrino 701 KF with Hydranal 2 (Sigma) Karl Fischer titration reagent. Reaction mixtures were filtrated under an inert atmosphere and 1.000 gram of the liquid sample was used for the Karl Fischer titration. The burette was rinsed with Hydranal 2 and the titration parameters were set as indicated below:

extraction time=9999 seconds
stop criterion=drift
stop at drift=15 (μL/min)
stop=40.0 mL
maximum speed=1.0 mL/min.
minimum volume increment=min (μL)
I(pol.)=10 μA
endpoint=75 mV
filling rate=20.0 mL/min.

Figure 4:
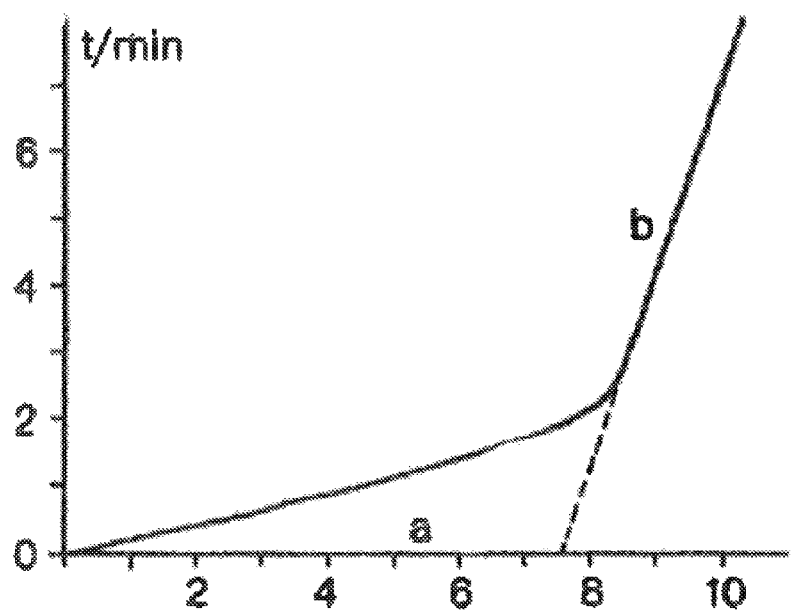
FIG. 4 illustrates the amount of Hydranal 2 solution as consumed over time.

100 mL of Hydranal solvent (Sigma) was introduced into the dry titration vessel and stirred with a magnetic bar. The Hydranal solvent was neutralized with Hydranal 2 until the consumption rate remained constant through time. 1.000 g of sample was introduced into the titration vessel and the sample was titrated with Hydranal 2. The amount of Hydranal 2 solution consumed was determined as in FIG. 4.

X-axis: titrant consumption
Y-axis: time scale titration

To infer the amount of standard volumetric solution consumed from the consumption/time curve:
- extend titration line b to the intersection with the X axis
- measure the perpendicular distance a from the intersection with the X axis to the Y axis as a measure of the amount of Hydranal 2 consumed (1 cm on the X-axis corresponds to 1 mL of titrant)

The amount of water (mass %) in the sample was calculated using the following formula.

$$(v*T_t)/(10*a)$$

Where:
$T_t$=mg of water equivalent to 1.00 mL of Hydranal 2 at t ° C.

Synthesis of Oligopeptide-OCam Esters (Oligopeptide Ester i))

The oligopeptide-OCam esters were synthesized using the following protocol:

1 gram of Sieber resin (Xanthenyl linker, with a loading of 0.5 mmol/gram) was washed with dichloromethane (10 mL, 2×2 min), 1-methyl-2-pyrrolidone (NMP, 10 mL, 2×2 min) and Fmoc-deprotected using piperidine/NMP (10 mL, 1/4, v/v, 2×8 min). After washing with NMP (10 mL, 2×2 min), dichloromethane (10 mL, 2×2 min) and NMP (10 mL, 2×2 min), iodoacetic acid (4 equiv.) was coupled to the resin using dicyclohexyl carbodiimide (DCC) (4 equiv.) in dichloromethane (10 mL, 45 min). After washing with NMP (10 mL, 2×2 min), dichloromethane (10 mL, 2×2 min) and THF (10 mL, 2×2 min), the resin was loaded with an Fmoc-protected amino acid (with the appropriate protecting group on the side chain functionality) using 4 equiv. Fmoc-Xxx-OH (wherein Xxx denotes an amino acid) and 10 equiv. DiPEA in DMF/THF (10 mL, 1/4, v/v) at 50° C. for 20 h. After washing with DMF (10 mL, 2×2 min), dichloromethane (10 mL, 2×2 min) and NMP (10 mL, 2×2 min), standard SPPS protocols (see Fmoc Solid Phase Peptide Synthesis by W. C. Chan and P. D. White, Oxford university press, 2004) were followed to elongate the peptide. Cleavage from the resin was performed using 2.5 vol % trifluoroacetic acid (TFA) in dichloromethane (10 mL per gram of resin) for 15 min. The resin was washed with dichloromethane and the combined filtrates were concentrated in vacuo to 1/3 of their original volume. Subsequently, isopropanol/water (1/3, v/v) was added and the mixture was concentrated in vacuo to 1/2 of their original volume. The precipitated oligopeptide-O-Cam-ester was filtered off and washed twice with water followed by lyophilisation from acetonitrile/water (3/1, v/v). Products were generally obtained in a yield >90% with a purity of >95% according to HPLC analysis.

| Product | NMR data |
|---|---|
| Ac-Asp(OtBu)-Leu-Ser(tBu)-Lys(Boc)-Gln(Trt)-OCam Seq. ID No: 1 | $^1$H NMR (DMSO-$d_6$, 300 MHz): δ = 0.84 (dd, J = 6.3 and 10.8 Hz, 6H), 1.09-2.55 (m, 43H), 2.70-2.77 (m, 1H), 3.44-3.46 (m, 2H), 4.16-4.41 (m, 6H), 4.53-4.57 (m, 1H), 6.76 (s, 1H), 7.08-7-34 (m, 19H), 7.75 (d, J = 7.2 Hz, 2H), 8.06 (d, J = 7.2 Hz, 1H), 8.24-8.32 (m, 2H), 8.53 (m, 1H). $^{13}$C NMR (DMSO-$d_6$, 75 MHz): δ = 21.5, 22.3, 22.9, 24.0, 27.1, 27.6, 28.2, 32.2, 37.2, 49.3, 51.1, 51.6, 52.0, 53.2, 61.3, 62.2, 69.1, 82.8, 77.2, 80.0, 126.2, 127.4, 128.4, 144.8, 155.4, 168.4, 169.0, 169.2, 170.5, 170.9, 171.2, 172.6. |
| Ac-Asp(OtBu)-Leu-Ser(tBu)-Lys(Boc)-Gln(Xan)-OCam Seq. ID No: 2 | $^1$H NMR (DMSO-$d_6$, 300 MHz): δ = 0.85 (dd, J = 6.6 and 12.6 Hz, 6H), 1.07-2.03 (m, 47H), 2.37-2.88 (m, 4H), 3.46 (d, J = 5.4 Hz, 2H), 4.06 (s, 2H), 4.28-4.57 (m, 5H), 4.60-4.65 (m, 1H), 6.75-7.06 (m, 2H), 7.06-7.36 (m, 10H), 7.72 (d, J = 7.8 Hz, 1H), 7.85 (d, J = 6.6 Hz, 1H), 7.97 (d, J = 8.1 Hz, 1H), 8.18 (d, J = 8.1 Hz, 1H), 8.36 (d, J = 6.6 Hz, 2H). |
| Ac-Asp(OtBu)-Leu-Ser(tBu)-Lys(Boc)-Gln-OCam Seq. ID No: 3 | $^1$H NMR (DMSO-$d_6$, 300 MHz): δ = 0.77 (dd, J = 6.3 and 11.4 Hz, 6H), 0.97-2.66 (m, 45H), 2.76-2.82 (m, 2H), 3.38-3.40 (m, 2H), 4.13-4.41 (m, 6H), 4.49-4.56 (m, 1H), 6.65-6.71 (m, 2H), 7.16-7.28 (m, 3H), 7.63 (d, J = 8.1 Hz, 1H), 7.76 (d, J = 7.5 Hz, 1H), 7.89 (d, J = 8.4 Hz, 1H), 8.09 (d, J = 8.1 Hz, 1H), 8.27 (d, J = 7.2 Hz, 2H). $^{13}$C NMR (DMSO-$d_6$, 75 MHz): δ = 21.5, 22.2, 22.3, 22.9, 26.5, 27.0, 27.6, 28.2, 29.1, 31.0, 37.2, 49.3, 51.2, 51.6, 52.0, 53.3, 61.3, 62.2, 72.8, 77.2, 80.0, 168.4, 169.1, 169.2, 170.5, 171.0, 171.6, 171.8, 176.2. |
| Ac-Phe-Ile-Glu(OtBu)-Trp(Boc)-Leu-OCam Seq. ID No: 4 | $^1$H NMR (DMSO-$d_6$, 300 MHz): δ = 0.79-0.89 (m, 12H), 0.98-1.16 (m, 1H), 1.29-1.90 (m, 28H), 2.14-2.22 (m, 2H), 2.66-3.10 (m, 4H), 4.09-4.20 (m, 1H), 4.23-4.39 (m, 4H), 4.45-4.57 (m, 1H), 4.80-4.89 (m, 1H), 7.16-7.35 (m, 9H), 7.50 (s, 1H), 7.67 (d, J = 7.8 Hz, 1H), 7.96-8.13 (m, 5H), 8.50 (d, J = 7.8 Hz, 1H). $^{13}$C NMR (DMSO-$d_6$, 75 MHz): δ = 15.7, 21.5, 22.8, 23.2, 24.4, 24.7, 28.1, 31.4, 36.8, 37.7, 50.6, 52.0, 52.5, 54.1, 57.2, 62.7, 80.0, 83.8, 115.0, 116.4, 119.7, 122.7, 124.2, 124.6, 126.5, 128.3, 129.5, 130.6, 135.0, 138.4, 149.4, 168.7, 169.5, 171.1, 171.4, 171.7, 171.9, 172.0. |

| Product | NMR data |
|---|---|
| Ac-Leu-Ser(tBu)-Lys(Boc)-Gln(Trt)-Met-OCam Seq. ID No: 5 | $^1$H NMR (DMSO-d$_6$, 300 MHz): δ = 0.85 (dd, J = 6.6 and 13.2 Hz, 6H), 1.15-2.03 (m, 39H), 2.30-2.36 (m, 2H), 2.83-2.90 (m, 2H), 3.49 (d, J = 5.7 Hz, 2H), 4.17-4.50 (m, 7H), 6.72-6.76 (m, 1H), 7.16-7-39 (m, 18H), 7.69 (d, J = 7.8 Hz, 1H), 7.86-7.93 (m, 2H), 8.09 (d, J = 7.8 Hz, 1H), 8.28 (d, J = 7.5 Hz, 1H), 8.56 (m, 1H). $^{13}$C NMR (DMSO-d$_6$, 75 MHz): δ = 14.9, 22.0, 22.8, 23.4, 27.6, 29.6, 51.4, 51.6, 52.8, 54.0, 61.7, 62.8, 69.6, 73.2, 126.7, 127.8, 128.9, 145.3, 168.7, 169.9, 171.4, 171.6, 171.7, 172.0, 172.8. |
| Ac-Glu(OtBu)-Glu(OtBu)-Ala-Val-Arg(Pbf)-OCam Seq. ID No: 6 | $^1$H NMR (DMSO-d$_6$, 300 MHz): δ = 0.89 (dd, J = 7.2 Hz, 6H), 1.22 (d, J = 7.5 Hz, 3H), 1.32-1.47 (m, 27H), 1.65-2.13 (m, 14H), 2.19-2.33 (m, 4H), 3.02-3.11 (m, 4H), 4.22-4.52 (m, 7H), 6.45-7.0 (m, 2H), 7.37 (d, J = 5.7 Hz, 1H), 7.81 (d, J = 18.9 Hz, 1H), 8.03-8.09 (m, 2H), 8.45 (d, J = 6.9 Hz, 1H). $^{13}$C NMR (DMSO-d$_6$, 75 MHz): δ = 17.6, 17.8, 18.8, 18.9, 22.3, 27.2, 27.6, 27.8, 28.1, 30.6, 31.0, 31.2, 42.3, 47.9, 51.3, 51.6, 51.8, 57.1, 62.2, 79.5, 86.1, 116.1, 124.2, 131.3, 137.1, 155.9, 157.3, 168.3, 169.3, 170.4, 171.0, 171.1, 171.2, 171.5, 171.6, 171.7. |
| Ac-Phe-Thr(tBu)-Ser(tBu)-Asp(OtBu)-Leu-OCam Seq. ID No: 7 | $^1$H NMR (DMSO-d$_6$, 300 MHz): δ = 0.84-1.77 (m, 41H), 2.40-3.10 (m, 4H), 3.44-3.65 (m, 2H), 3.95-4.00 (m, 1H), 4.23-4.42 (m, 5H), 4.58-4.72 (m, 2H), 7.19-7.34 (m, 7H), 7.66 (d, J = 7.2 Hz, 1H), 7.81 (d, J = 7.8 Hz, 1H), 8.03 (d, J = 8.4 Hz, 1H), 8.19-8.27 (m, 2H). $^{13}$C NMR (DMSO-d$_6$, 75 MHz): δ = 18.9, 21.7, 22.7, 23.2, 24.4, 27.5, 28.0, 28.4, 37.4, 38.0, 49.6, 50.8, 53.7, 54.3, 58.0, 62.1, 62.7, 66.9, 73.3, 74.4, 80.6, 126.6, 128.4, 129.5, 138.4, 168.7, 169.3, 169.4, 169.5, 169.7, 170.7, 171.8, 171.9. |
| Ac-Leu-Asp(OtBu)-Gln(Trt)-Ser(tBu)-Gln-OCam Seq. ID No: 8 | $^1$H NMR (DMSO-d$_6$, 300 MHz): δ = 0.85 (dd, J = 6.6 and 11.1 Hz, 6H), 1.10-2.36 (m, 30H), 2.71-2.80 (m, 1H), 3.46 (d, J = 5.4 Hz, 2H), 4.19-4.59 (m, 7H), 6.78 (s, 1H), 7.09-7.36 (m, 19H), 7.76 (d, J = 6.3 Hz, 1H), 8.07 (d, J = 6.6 Hz, 1H), 8.25-8.34 (m, 2H), 8.55 (s, 1H). |

Synthesis of Fmoc-Ala-O—CH$_2$—COOH 1 mmol of Fmoc-Ala-OH was dissolved in 100 mL anhydrous THF/DMF (8/2, v/v) followed by the addition of 2 equivalents of tert-butyl 2-iodoacetate and 2.5 equivalents of DiPEA. This mixture was shaken at 50° C. with 150 rpm for 20 h. Then, the volatiles were removed in vacuo and the residue redissolved in a mixture of 250 mL EtOAc and 250 mL of saturated aqueous NaHCO$_3$. The two phases were separated and the organic layer was washed with saturated aqueous NaHCO$_3$ (250 mL, 1×), aqueous HCl (250 mL, pH 1, 2×), brine (250 mL, 1×), dried over Na$_2$SO$_4$, concentrated in vacuo and the volatiles were co-evaporated with toluene (50 mL, 2×) and CHCl$_3$ (50 mL, 2×). Subsequently, 10 mL of TFA/H$_2$O (95/5, v/v) was added and the mixture was stirred for 1 h followed by the addition of 100 mL IPA/H$_2$O (1/3, v/v). 50 mL of the volatiles were removed in vacuo and the precipitates were filtered off and washed with 50 mL of H$_2$O (2×). The remaining crude ester was purified by preparative HPLC and obtained in 52% yield with a purity of >98% according to HPLC analysis.

Synthesis of Fmoc-Gln(Trt)-O—CH$_2$—COOH 1 mmol of Fmoc-Gln(Trt)-OH was dissolved in 100 mL anhydrous THF/DMF (8/2, v/v) followed by the addition of 2 equivalents of benzyl-2-iodoacetate and 2.5 equivalents of DiPEA. This mixture was shaken at 50° C. with 150 rpm for 20 h. Then, the volatiles were removed in vacuo and the residue redissolved in a mixture of 250 mL EtOAc and 250 mL of saturated aqueous NaHCO$_3$. The two phases were separated and the organic layer was washed with saturated aqueous NaHCO$_3$ (250 mL, 1×), aqueous HCl (250 mL, pH 1, 2×), brine (250 mL, 1×), dried over Na$_2$SO$_4$, concentrated in vacuo and the volatiles were co-evaporated with toluene (50 mL, 2×) and CHCl$_3$ (50 mL, 2×). The residue was dissolved in 250 mL MeOH/toluene (1/1, v/v) followed by hydrogenolysis overnight at 25° C. with 5 bar H$_2$ using 1 gram of 10% Pd/C. After removal of the solids by filtration, the volatiles were removed in vacuo. The resulting crude ester was purified by preparative HPLC and obtained in 63% yield with a purity of >98% according to HPLC analysis.

Synthesis of Oligopeptide-OCam-Xxx-NH$_2$ Esters (Oligopeptide Ester i) with R$_2$ an Amino Acid Residue with a C-Terminal Carboxyamide Functionality)

1 gram of Sieber resin (Xanthenyl linker, with a loading of 0.5 mmol/gram) was washed with dichloromethane (10 mL, 2×2 min), NMP 10 mL, (2×2 min) and Fmoc-deprotected using piperidine/NMP (10 mL, 1/4, v/v, 2×8 min). After washing with NMP (10 mL, 2×2 min), dichloromethane (10 mL, 2×2 min) and NMP (10 mL, 2×2 min), Fmoc-Xxx-OH (4 equiv.) was coupled to the resin using HBTU (4 equiv.), HOBt (4 equiv.) and DiPEA (8 equiv.) in NMP (10 mL, 45 min). After washing with NMP (10 mL, 2×2 min), dichloromethane (10 mL, 2×2 min) and NMP (10 mL, 2×2 min), the amino acid was Fmoc-deprotected using piperidine/NMP (10 mL, 1/4, v/v, 2×8 min) the resin was washed with NMP (10 mL, 2×2 min), dichloromethane (10 mL, 2×2 min) and NMP (10 mL, 2×2 min), followed by coupling of Fmoc-Xxx-O—CH$_2$—COOH (2 equiv.) using HBTU (2 equiv.), HOBt (2 equiv.) and DiPEA (4 equiv.) in NMP (10 mL, 90 min). After washing with NMP (10 mL, 2×2 min), dichloromethane (10 mL, 2×2 min) and NMP (10 mL, 2×2 min), standard SPPS protocols (see Fmoc Solid Phase Peptide Synthesis by W. C. Chan and P. D. White, Oxford university press, 2004) were followed to elongate the peptide. Cleavage and purification of the oligopeptide-OCam-Xxx-NH$_2$ esters was identical to protocol 2. Products were generally obtained in a yield >90% with a purity of >95% according to HPLC analysis.

| Product | NMR data |
|---|---|
| Fmoc-Val-Ala-OCam-Ala-NH$_2$ | $^1$H NMR (DMSO-d$_6$, 300 MHz): δ = 0.87 (t, 6H, J = 7.2 Hz), 1.32 (d, 3H, J = 7.2 Hz), 1.87-2.15 (m, 5H), 2.77-2.85 (m, 1H), 2.99-3.05 (m, 1H), 3.89 (t, 1H, J = 8.1 Hz), 4.20-4.61 (m, 6H), 7.12-7.46 (m, 11H), 7.72-7.76 (m, 2H), 7.90 (d, 2H, J = 7.5 Hz), 8.09 (d, 1H, J = 8.4 Hz), 8.44 (d, 1H, J = 6.3 Hz). $^{13}$C NMR (DMSO-d$_6$, 75 MHz): δ = 16.6, 18.2, 19.0, 30.3, 46.6, 47.5, 47.7, 59.6, 62.3, 65.6, 120.0, 125.3, 126.9, 127.5, 140.6, 143.7, 143.8, 155.9, 165.8, 171.3, 171.9, 173.7. |
| Fmoc-Val-Ala-OCam-Arg(Pbf)-NH$_2$ | $^1$H NMR (DMSO-d$_6$, 300 MHz): δ = 0.86 (t, 6H, J = 6.9 Hz), 1.10 (s, 4H), 1.32-1.40 (m, 9H), 2.00 (s, 3H), 3.81-3.93 (m, 1H), 4.17-4.35 (m, 5H), 4.53 (q, 2H, J = 14.7 Hz and 6 Hz), 7.07 (s, 1H), 7.28-7.43 (m, 5H), 7.75 (q, 2H, J = 4.8 Hz and 2.4 Hz), 7.88 (d, 2H, 7.5 Hz), 7.99 (d, 1H, J = 8.1 Hz), 8.45 (d, 1H, J = 6.3 Hz). $^{13}$C NMR (DMSO-d$_6$, 75 MHz): δ = 12.1, 16.7, 17.5, 18.1, 18.8, 19.0, 28.2, 30.3, 31.2, 42.4, 46.6, 47.4, 51.6, 59.6, 62.2, 65.6, 86.2, 116.1, 120.0, 124.2, 125.3, 126.9, 127.5, 131.3, 137.2, 140.6, 143.7, 143.8, 156.0, 157.3, 166.1, 171.3, 171.9, 173.0. |
| Fmoc-Val-Ala-OCam-Asn(Trt)-NH$_2$ | $^1$H NMR (DMSO-d$_6$, 300 MHz): δ = 0.88 (q, 5H, J = 6.6 Hz and 5.4 Hz), 1.11 (s, 1H), 1.32 (d, 2H, J = 7.2 Hz), 1.97 (t, 1H, J = 6.6 Hz), 3.79-3.94 (m, 1H), 4.17-4.33 (m, 3H), 4.44-4.61 (m, 2H), 7.11-7.43 (m, 17H), 7.74 (q, 1H, J = 4.5 Hz and 2.1 Hz), 7.89 (d, 2H, J = 7.5 Hz), 8.23 (d, 1H, J = 8.1 Hz), 8.46 (d, 1H, J = 6.3 Hz), 8.59 (s, 1H). $^{13}$C NMR (DMSO-d$_6$, 75 MHz): δ = 16.7, 18.1, 19.0, 30.4, 46.6, 47.5 49.6, 62.1, 65.6, 69.3, 120.0, 125.3, 126.2, 126.9, 127.3, 127.5, 128.4, 140.6, 144.6, 166.0, 168.9, 171.3, 171.9, 172.0. |
| Fmoc-Val-Ala-Ocam-Asp(OtBu)-NH$_2$ | $^1$H NMR (DMSO-d$_6$, 300 MHz): δ = 0.87 (t, 6H, J = 7.5 Hz), 1.11 (s, 2H), 1.37 (s, 12H), 1.97 (q, 1H, J = 6.6 Hz and 6.3 Hz), 2.63-2.70 (m, 1H), 3.90 (t, 1H, J = 8.1 Hz), 4.17-4.58 (m, 7H), 7.15 (s, 1H), 7.31-7.44 (m, 6H), 7.73 (s, 2H), 7.89 (d, 2H, J = 7.5 Hz), 8.18 (d, 1H, J = 8.1), 8.45 (d, 1H, J = 6.3). $^{13}$C NMR (DMSO-d$_6$, 75 MHz): δ = 16.7, 18.1, 19.0, 27.5, 30.3, 31.2, 37.4, 46.6, 47.5, 49.0, 59.6, 62.2, 65.6, 80.0, 120.0, 125.3, 126.9, 127.5, 140.6, 143.7, 143.8, 156.0, 166.1, 169.3, 171.3, 171.8. |
| Fmoc-Val-Ala-OCam-Cys(Trt)-NH$_2$ | $^1$H NMR (DMSO-d$_6$, 300 MHz): δ = 0.87 (q, 6H, J = 6.9 Hz and 2.4 Hz), 1.34 (d, 2H, J = 7.2 Hz), 1.98 (q, 1H, J = 6.9 Hz), 3.90 (t, 1H, J = 8.1 Hz), 4.13-4.38 (m, 4H), 4.48-4.64 (m, 2H), 6.43-7.10 (m, 20H), 7.46-7.76 (m, 2H), 7.89 (d, 2H, J = 6.0 Hz), 8.20 (d, 1H, J = 8.4 Hz), 8.44 (d, 1H, J = 6.9 Hz). $^{13}$C NMR (DMSO-d$_6$, 75 MHz): δ = 14.0, 14.3, 16.7, 18.1, 18.2, 19.0, 22.1, 30.3, 33.8, 46.6, 47.4, 55.7, 120.0, 125.3, 126.1, 126.6, 126.9, 127.4, 127.5, 127.7, 127.9, 128,2 128.9, 129.0, 140.6, 143.7, 143.8, 144.1, 166.0, 171.1, 171.8 |
| Fmoc-Val-Ala-OCam-Glu(OtBu)-NH$_2$ | $^1$H NMR (DMSO-d$_6$, 300 MHz): δ = 0.88 (t, 6H, J = 7.2 Hz), 1.11 (s, 1H), 1.33-1.39 (m, 12H), 1.66-1.79 (m, 1H), 1.87-2.02 (m, 2H), 2.17-2.27 (m, 2H), 3.90 (q, 1H, J = 7.2 Hz), 4.17-4.37 (m, 5H), 4.54 (q, 2H, J = 14.7 Hz and 7.5 Hz), 7.11 (s, 1H), 7.29-7.44 (m, 6H), 7.74 (q, 2H, J = 4.5 Hz and 2.7 Hz), 7.89 (d, 2H, J = 7.5 Hz), 8.00 (d, 1H, J = 8.1 Hz), 8.46 (d, 1H, J = 6.3 Hz). NMR $^{13}$C NMR (DMSO-d$_6$, 75 MHz): δ = 16.7, 18.1, 19.0, 28.0, 30.3, 31.2, 32.5, 46.6, 47.5, 51.9, 59.6, 62.2, 65.6, 69.1, 120.0, 125.3, 126.2, 126.9, 127.3, 127.4, 127.5, 128.4, 140.6, 143.7, 143.8, 144.8, 166.1, 171.2, 171.3, 171.9, 172.0. |
| Fmoc-Val-Ala-OCam-Gln(Trt)-NH$_2$ | $^1$H NMR (DMSO-d$_6$, 300 MHz): δ = 0.80 (q, 6H, J = 6.6 Hz and 3.9 Hz), 1.04 (s, 1H), 1.26 (d, 3H, J = 7.2 Hz), 1.55-1.68 (m, 1H), 1.74-1.93 (m, 2H), 2.20-2.25 (m, 2H), 3.83 (q, 1H, J = 16.2 Hz and 7.5 Hz), 4.06-4.28 (m, 5H), 4.47 (q, 2H, J = 14.7 Hz and 10.2 Hz), 7.00-7.37 (m, 13H), 7.67 (q, 2H, J = 3.6 Hz), 7.82 (d, 2H, J = 7.5 Hz), 7.96 (d, 1H, J = 8.1 Hz), 8.37 (d, 1H, J = 6.6 Hz), 8.54 (s, 1H). $^{13}$C NMR (DMSO-d$_6$, 75 MHz): δ = 16.6, 18.1, 19.0, 27.2, 27.6, 30.3, 31.1, 46.6, 47.6, 51.3, 59.6, 62.2, 65.6, 79.6, 120.0, 125.3, 126.9, 127.5, 140.6, 143.7, 143.8, 155.9, 166.2, 171.3, 171.5, 171.9, 172.6. |
| Fmoc-Val-Ala-OCam-Gly-NH$_2$ | $^1$H NMR (DMSO-d$_6$, 300 MHz): δ = 0.88 (t, 6H, J = 7.2 Hz), 1.34 (d, 3H, J = 6.9 Hz), 1.93-2.00 (m, 1H), 3.66 (d, 2H, J = 5.4 Hz), 3.90 (t, 1H, J = 7.8 Hz), 4.22-4.59 (m, 6H), 7.08 (s, 1H), 7.30-7.44 (m, 6H), 7.74-7.90 (m, 4H), 8.14 (s, 1H), 8.47 (d, 1H, J = 6.3 Hz). $^{13}$C NMR (DMSO-d$_6$, 75 MHz): δ = 16.7, 18.1, 19.0, 30.3, 41.5, 46.6, 47.5, 59.6, 62.4, 65.6, 120.0, 125.3, 126.9, 127.5, 140.6, 143.7, 143.8, 156.0, 166.6, 170.4, 171.3, 171.9. |

| Product | NMR data |
|---|---|
| Fmoc-Val-Ala-OCam-His(Trt)-NH$_2$ | $^1$H NMR (DMSO-d$_6$, 300 MHz): δ = 0.85 (t, 6H, J = 6.0 Hz), 1.30 (d, 3H, J = 7.2 Hz), 1.94 (q, 1H, J = 6.9 Hz), 2.73-2.84 (m, 1H), 2.92-3.10 (m, 2H), 3.89 (q, 1H, J = 7.5 Hz and 1.2 Hz), 4.17-4.32 (m, 3H), 4.57-4.58 (m, 3H), 6.97 (s, 1H), 7.09-7.44 (m, 24H), 7.73 (q, 2H, J = 4.5 and 2.4 Hz), 7.89 (d, 2H, J = 7.5 Hz), 8.14 (d, 2H, J = 8.1), 8.46 (d, 1H, J = 6.3). $^{13}$C NMR (DMSO-d$_6$, 75 MHz): δ = 16.6, 18.1, 18.9, 30.3, 46.6, 47.5, 51.5, 55.7, 59.6, 62.1, 65.6, 120.0, 120.2, 125.3, 126.1, 126.5, 126.9, 127.4, 127.5, 127.6, 128.2, 128.4, 128.4, 128.9, 129.1, 136.7, 140.6, 140.8, 143.7, 143.8, 166.1, 171.3, 171.8, 171.8. |
| Fmoc-Val-Ala-OCam-Ile-NH$_2$ | $^1$H NMR (DMSO-d$_6$, 300 MHz): δ = 0.79-0.93 (m, 12H), 1.01-1.44 (m, 7H), 1.68-1.75 (m, 2H), 1.93-2.00 (m, 1H), 3.89 (t, 1H, J = 8.1 Hz), 4.13-4.35 (m, 5H), 4.48-4.71 (m, 2H), 7.05 (s, 1H), 7.29-7.44 (m, 6H), 7.72-7.90 (m, 5H), 8.45 (d, 1H, J = 6.6). $^{13}$C NMR (DMSO-d$_6$, 75 MHz): δ = 11.0, 15.3, 16.7, 18.1, 190.0, 24.0, 30.3, 36.5, 46.6, 47.4, 56.3, 59.6, 62.2, 65.6, 120.0, 125.3, 126.9, 127.5, 140.6, 143.7, 143.8, 155.9, 166.0, 171.2, 171.9, 172.5. |
| Fmoc-Val-Ala-OCam-Leu-NH$_2$ | $^1$H NMR (DMSO-d$_6$, 300 MHz): δ = 0.82-0.90 (m, 12H), 1.33-1.61 (m, 5H), 1.97 (q, 1H, J = 6.9 Hz), 3.89 (q, 1H, J = 7.5 Hz and 1.5 Hz), 4.18-4.38 (m, 5H), 4.53 (q, 2H, J = 14.7 Hz and 5.4 Hz), 7.01 (s, 1H), 7.29-7.44 (m, 1H), 7.74 (q, 2H, J = 4.5 and 2.4 Hz), 7.88-7.98 (m, 3H), 8.46 (d, 1H, J = 6.0 Hz). $^{13}$C NMR (DMSO-d$_6$, 75 MHz): δ = 16.7, 18.1, 19.0, 21.4, 22.9, 24.1, 30.3, 40.8, 46.6, 47.8, 50.5, 59.6, 62.2, 65.6, 120.0, 125.3, 126.9, 127.5, 140.6, 143.7, 143.8, 155.9, 166.0, 171.3, 171.9, 173.6. |
| Fmoc-Val-Ala-OCam-Lys(Boc)-NH$_2$ | $^1$H NMR (DMSO-d$_6$, 300 MHz): δ = 0.862 (t, 6H, J = 7.5 Hz), 1.32-1.35 (m, 12H), 1.95 (q, 1H, J = 6.9 Hz), 2.86 (q, 2H, J = 6.3 Hz), 3.80-3.91 (m, 1H), 4.12-4.34 (m, 4H), 4.52 (q, 2H, J = 14.7 Hz and 6.3 Hz), 6.27 (s, 1H), 6.73 (s, 1H), 7.28-7.43 (m, 5H), 7.71-7.95 (m, 5H), 8.45 (d, 1H, J = 6.6 Hz). $^{13}$C NMR (DMSO-d$_6$, 75 MHz): δ = 12.1, 16.7, 17.5, 18.1, 18.8, 190.0, 22.5, 28.2, 29.1, 30.3, 31.1, 46.6, 47.5, 51.6, 59.6, 62.2, 65.6, 86.2, 120.0, 124.2, 125.3, 126.9, 127.5, 128.8, 131.3, 140.6, 143.7, 143.8, 156.0, 166.1, 171.3, 171.9, 173.0. |
| Fmoc-Val-Ala-OCam-Met-NH$_2$ | $^1$H NMR (DMSO-d$_6$, 300 MHz): δ = 0.87 (t, 5H, J = 7.5 Hz), 1.10-1.35 (m, 3H), 1.93-2.02 (m, 4H), 3.82-3.92 (m, 1H), 4.20-4.35 (m, 4H), 4.54 (q, 2H, J = 14.7 Hz and 5.1 Hz), 7.10 (s, 1H), 7.29-7.43 (m, 5H), 7.74 (q, 2H, J = 3.6 Hz), 7.88 (d, 2H, J = 7.5 Hz), 8.04 (d, 2H, J = 8.1 Hz), 8.47 (d, 1H, J = 6.3 Hz). $^{13}$C NMR (DMSO-d$_6$, 75 MHz): δ = 14.5, 16.6, 18.1, 19.0, 29.5, 30.3, 31.7, 46.5, 47.5, 51.3, 59.6, 62.3, 65.6, 120.0, 125.3, 126.9, 127.5, 140.6, 143.7, 143.8, 155.9, 166.3, 171.3, 172.0, 172.7. |
| Fmoc-Val-Ala-OCam-Phe-NH$_2$ | $^1$H NMR (DMSO-d$_6$, 300 MHz): δ = 0.87 (t, 6H, J = 7.5 Hz), 1.32 (d, 3H, J = 7.2 Hz), 1.87-2.15 (m, 5H), 2.81 (q, 1H, J = 9.0 Hz and 4.5 Hz), 2.99-3.05 (m, 1H), 3.89 (t, 1H, J = 8.1 Hz), 4.20-4.46 (m, 7H), 7.11-7.46 (m, 11H), 7.72-7.76 (m, 2H), 7.89 (d, 2H, J = 7.5 Hz), 8.09 (d, 1H, J = 8.4 Hz), 8.44 (d, 1H, J = 6.3 Hz). $^{13}$C NMR (DMSO-d$_6$, 75 MHz): δ = 16.7, 18.1, 19.0, 30.3, 37.5, 46.6, 47.5, 53.5, 59.6, 62.1, 65.6, 120.0, 125.3, 126.1, 126.9, 127.5, 129.0, 137.7, 140.6, 143.7, 143.8, 166.0, 171.1, 171.7, 172.4. |
| Fmoc-Val-Ala-OCam-Pro-NH$_2$ | $^1$H NMR (DMSO-d$_6$, 300 MHz): δ = 0.85-0.91 (m, 6H), 1.36 (d, 3H, J = 7.2 Hz), 1.78-20.3 (m, 5H), 3.90 (t, 1H, J = 8.1 Hz), 4.15-4.45 (m, 5H), 4.61-4.89 (m, 1H), 6.94 (s, 1H), 7.22-7.44 (m, 6H), 7.73-7.77 (m, 2H), 7.89 (d, 2H, J = 7.5 Hz), 8.39 (d, 1H, J = 6.3). $^{13}$C NMR (DMSO-d$_6$, 75 MHz): δ = 16.8, 18.2, 19.0, 24.0, 29.0, 30.3, 45.1, 46.6, 47.3, 59.6, 61.6, 65.6, 120.0, 125.3, 126.9, 127.5, 140.6, 143.7, 143.8, 155.9, 164.6, 171.1, 171.9, 173.3. |
| Fmoc-Val-Ala-OCam-Ser(tBu)-NH$_2$ | $^1$H NMR (DMSO-d$_6$, 300 MHz): δ = 0.87 (t, 6H, J = 7.8 Hz), 1.10 (s, 10H), 1.35 (d, 3H, J = 7.2 Hz), 1.94-2.00 (m, 1H), 3.90 (t, 1H, J = 8.1 Hz), 4.20-4.36 (m, 5H), 4.50-4.63 (m, 2H), 7.11 (s, 1H), 7.29-7.44 (m, 6H), 7.73-7.75 (m, 2H), 7.89 (d, 3H, J = 7.5 Hz). $^{13}$C NMR (DMSO-d$_6$, 75 MHz): δ = 16.7, 18.1, 19.0, 27.1, 30.3, 31.2, 46.6, 47.4, 52.9, 59.6, 61.7, 62.2, 65.6, 72.6, 120.0, 125.3, 126.9, 127.5, 140.6, 143.7, 156.0, 166.1, 171.2, 171.2, 171.2. |
| Fmoc-Val-Ala-OCam-Thr(tBu)-NH$_2$ | $^1$H NMR (DMSO-d$_6$, 300 MHz): δ = 0.88 (q, 6H, J = 6.9 Hz and 2.4 Hz), 1.00 (d, 3H, J = 6.3 Hz), 1.13 (s, 9H), 1.23 (d, 1H, J = 6.9 Hz), 1.35 (d, 3H, J = 7.2 Hz), 1.97 (q, 1H, J = 6.9 Hz), 3.84-3.98 (m, 2H), 4.13-4.36 (m, 5H), 4.52-4.69 (m, 2H), 7.16-7.44 (m, 7H), 7.62-7.76 (m, 3H), 7.89 (d, 2H, J = 7.5 Hz), 8.43 (d, 1H, J = 6.6 Hz). $^{13}$C NMR (DMSO-d$_6$, 75 MHz): δ = 16.8, 171.1, 19.0, 19.4, 27.9, 30.3, 46.6, 47.4, 57.3, 59.6, 62.3, 65.6, 66.7, 73.4, 120.0, 120.0, 121.3, 125.3, 126.9, 127.2, 127.5, 128.8, 140.6, 143.7, 143.8, 155.9, 166.2, 171.1, 171.2, 171.4, 171.7. |

| Product | NMR data |
|---|---|
| Fmoc-Val-Ala-OCam-Trp(Boc)-NH$_2$ | $^1$H NMR (DMSO-d$_6$, 300 MHz): δ = 0.84 (t, 6H, J = 6.9 Hz), 1.31, (d, 3H, J = 7.2 Hz), 1.61 (s, 8H), 1.93 (q, 1H, J = 6.9 Hz), 2.94 (q, 1H, J = 8.4 Hz and 6.6 Hz), 3.12 (q, 1H, J = 9.9 Hz and 4.8 Hz), 3.88 (t, 1H, J = 8.4 Hz), 4.20-4.58 (m, 6H), 7.18-7.81 (m, 13H), 7.88 (d, 2H, J = 7.5 Hz), 8.02 (d, 1H, J = 8.1), 8.18 (d, 1H, J = 8.1 Hz), 8.44 (d, 1H, J = 6.3). $^{13}$C NMR (DMSO-d$_6$, 75 MHz): δ = 16.6, 18.1, 18.9, 27.2, 27.6, 30.3, 46.6, 47.5, 52.0, 59.6, 62.1, 65.6, 83.3, 114.5, 116.4, 119.2, 120.0, 122.3, 123.7, 124.1, 125.6, 126.9, 127.5, 130.2, 134.5, 140.6, 143.7, 143.8, 148.9, 155.9, 166.1, 171.2, 171.7, 172.4. |
| Fmoc-Val-Ala-OCam-Ty(tBu)-NH$_2$ | $^1$H NMR (DMSO-d$_6$, 300 MHz): δ = 0.85-0.89 (m, 6H), 1.25 (s, 7H), 1.32 (d, 3H, J = 7.5), 1.97 (q, 1H, J = 6.9 Hz), 2.72-3.01 (m, 2H), 3.89 (q, 1H, J = 7.5 Hz and 1.5 Hz), 4.17-4.45 (m, 7H), 6.61-6.84 (m, 2H), 6.98-7.12 (m, 3H), 7.29-7.44 (m, 6H), 7.72-7.76 (m, 2H), 7.89 (d, 2H, J = 7.5 Hz), 7.99-8.07 (m, 2H), 8.45 (d, 1H, J = 6.3). $^{13}$C NMR (DMSO-d$_6$, 75 MHz): δ = 16.1, 17.6, 18.4, 27.9, 29.7, 46.0, 46.9, 52.9, 59.1, 61.5, 65.0, 76.9, 114.2, 119.3, 122.6, 124.7, 126.4, 127.0, 129.0, 129.4, 131.7, 140.0, 143.1, 143.2, 152.7, 155.4, 165.4, 170.7, 171.1, 171.9. |
| Fmoc-Val-Ala-OCam-Val-NH$_2$ | $^1$H NMR (DMSO-d$_6$, 300 MHz): δ = 0.81-0.90 (m, 12H), 1.34 (d, 3H, J = 7.2 Hz), 1.91-2.04 (m, 2H), 3.89 (q, 1H, J = 7.5 Hz and 1.2 Hz), 4.11-4.38 (m, 5H), 4.56 (q, 2H, J = 14.4 Hz), 7.06 (s, 1H), 7.29-7.44 (m, 6H), 7.72-7.90 (m, 5H), 8.45 (d, 1H, J = 6.6 Hz). $^{13}$C NMR (DMSO-d$_6$, 75 MHz): δ = 16.7, 17.7, 18.1, 19.0, 19.1, 30.3, 46.6, 47.4, 57.1, 59.6, 62.2, 65.6, 120.0, 125.3, 126.7, 127.5, 140.6, 143.7, 143.8, 155.9, 166.1, 171.2, 171.8, 172.5. |
| Ac-Asp(OtBu)-Leu-Ser(tBu)-Lys(Boc)-Gln(Trt)-OCam-Leu-NH$_2$ | $^1$H NMR (DMSO-d$_6$, 300 MHz): δ = 0.74-0.80 (m, 12H), 1.02-196 (m, 45H), 1.05-2.85 (m, 4H), 4.15-4.56 (m, 8H), 6.63-6.66 (m, 1H), 6.93 (s, 1H), 6.98-7.29 (m, 16H), 7.60 (d, J = 7.8 Hz, 1H), 7.76 (d, J = 7.8 Hz, 1H), 7.87 (d, J = 8.1 Hz, 1H), 7.95 (d, J = 8.4 Hz, 1H), 8.09 (d, J = 8.1 Hz, 1H), 8.22 (d, J = 6.9 Hz, 1H), 8.48 (s, 1H). $^{13}$C NMR (DMSO-d$_6$, 75 MHz): δ = 21.4m 21.5, 22.3, 22.9, 24.0, 24.1, 27.1, 27.5, 28.2, 69.1, 72.7, 80.0, 126.2, 127.3, 128.4, 144.7, 166.1, 169.0, 169.1, 169.2, 170.5, 170.9, 171.2, 171.5, 171.8, 176.2. |
| Fmoc-Val-Gln(Trt)-OCam-Gly-NH$_2$ | $^1$H NMR (DMSO-d$_6$, 300 MHz): δ = 0.06 (s, 2H), 0.88-0.97 (m, 8H), 1.11-1.15 (m, 3H), 1.24 (s, 2H), 1.62-1.98 (m, 5H), 2.28-2.42 (m, 3H), 3.51-3.66 (m, 5H), 3.91 (t, 1H, J = 7.5 Hz), 4.14-4.33 (m, 5H), 4.53-4.60 (m, 2H), 7.06-7.40 (m, 25H), 7.66-7.75 (m, 2H), 7.88 (d, 1.91, J = 7.5 Hz), 8.21 (s, 1H), 8.44-8.54 (m, 1H). $^{13}$C NMR (DMSO-d$_6$, 75 MHz): δ = 17.0, 18.2, 19.0, 46.5, 51.5, 62.1, 65.6, 69.1, 109.6, 120.0, 121.3, 125.3, 126.2, 126.9, 127.2, 127.3, 127.5, 128.4, 128.8, 140.6, 143.6, 143.8, 144.7, 144.8, 156.0, 166.7, 166.9, 170.7, 171.0, 171.1, 171.7. |

Synthesis of Oligopeptide-OCam-Xxx-OH Esters (Oligopeptide Ester i) with R$_2$ an Amino Acid Residue with a C-Terminal Carboxylic Acid Functionality)

1 gram of Trityl resin (2-chloro-chlorotrityl linker, with a loading of 1.0 mmol/gram) was washed with dichloromethane (10 mL, 2×2 min) and Fmoc-Xxx-OH (2 equiv.) was coupled to the resin using DiPEA (5 equiv.) in dichloromethane (10 mL, 30 min). After washing with DMF (10 mL, 2×2 min), the unreacted chlorotrityl groups were capped using dichloromethane/MeOH/DiPEA (10 mL, 80/15/5, v/v/v, 2×10 min). After washing with NMP (10 mL, 2×2 min), dichloromethane (10 mL, 2×2 min) and NMP (10 mL, 2×2 min), the amino acid was Fmoc-deprotected using piperidine/NMP (10 mL, 1/4, v/v, 2×8 min) followed by coupling of iodoacetic acid (4 equiv.) using DCC (4 equiv.) in dichloromethane (10 mL, 45 min). After washing with NMP (10 mL, 2×2 min), dichloromethane (10 mL, 2×2 min) and THF (10 mL, 2×2 min), the resin was treated with Fmoc-Xxx-OH (4 equiv.) and 10 equiv. DiPEA in DMF/THF (10 mL, 1/4, v/v) at 50° C. for 20 h. After washing with DMF (10 mL, 2×2 min), dichloromethane (10 mL, 2×2 min) and NMP (10 mL, 2×2 min), standard SPPS protocols (see Fmoc Solid Phase Peptide Synthesis by W. C. Chan and P. D. White, Oxford university press, 2004) were followed to elongate the peptide. Cleavage and purification of the oligopeptide-OCam-Xxx-OH esters was identical to protocol 2. Products were generally obtained in a yield >90% with a purity of >95% according to HPLC analysis.

| Product | NMR data |
|---|---|
| Fmoc-Val-Ala-Cam-Leu-OH | $^1$H NMR (DMSO-d$_6$, 300 MHz): δ = 0.85-0.87 (m, 12H), 1.34 (d, 3H, J = 3.5 Hz), 1.54-1.60 (m, 3H), 1.98 (t, 1H, J = 6 Hz), 3.87-3.92 (m, 1H), 4.22-4.36 (m, 5H), 4.46-4.60 (m, 2H), 7.32-7.44 (m, 5H), 7.74 (s, 2H), 7.89 (d, 2H, J = 3.6 Hz), 8.15 (d, 1H, J = 3.6 Hz), 8.46 (d, 1H, J = 2.7 Hz). $^{13}$C NMR (DMSO-d$_6$, 75 MHz): δ = 18.2, 19.0, 21.4, 22.9, 24.1, 30.3, 46.6, 50.5, 51.5, 59.7, 62.3, 65.6, 69.1, 120.0, 125.2, 126.2, 126.9, 127.3, 127.5, 128.2, 128.4, 140.6, 143.6, 143.8, 144.7, 156.0, 166.1, 170.9, 171.3, 171.6, 173.6. |

-continued

| Product | NMR data |
| --- | --- |
| Fmoc-Val-Gln(Trt)-Cam-Gly-OH | ¹H NMR (DMSO-d$_6$, 300 MHz): δ = 0.06 (s, 1H), 0.88 (s, 6H), 1.41 (d, 1H, J = 300 Hz), 1.82-1.84 (m, 2H), 1.97 (d, 2H, J = 6.9 Hz), 3.77-3.79 (m, 2H), 3.92 (t, 1H, J = 7.5 Hz), 4.33-4.48 (m, 4H), 4.54 (q, 2H, J = 15.3 Hz and 6.9 Hz), 7.17-7.41 (m, 19H), 7.66-7.75 (m, 2H), 7.89 (d, 2H, J = 7.2 Hz), 8.31 (s, 1H), 8.44 (d, 1H, J = 2.7 Hz), 8.62 (s, 1H) |

Synthesis of Oligopeptide C-Terminal Amide Nucleophiles (Oligopeptide Nucleophile ii))

Oligopeptide C-terminal amide nucleophiles were synthesized on a Sieber resin (Xanthenyl linker, with a loading of 0.5 mmol/gram) using standard SPPS protocols (see Fmoc Solid Phase Peptide Synthesis by W. C. Chan and P. D. White, Oxford university press, 2004). Cleavage from the resin was performed using 2.5 vol % trifluoroacetic acid (TFA) in dichloromethane (10 mL per gram of resin) for 15 min. The resin was washed twice with 10 mL dichloromethane and the combined filtrates were washed twice with 10 mL saturated aqueous NaHCO$_3$ followed by concentration to 1/3 of their original volume in vacuo. Precipitation, washing and drying were identical to protocol 2. Products were generally obtained in a yield >90% with a purity of >95% according to HPLC analysis.

| Product | NMR data |
| --- | --- |
| H-Phe-Val-Gly-Ser(tBu)-Arg(Pbf)-NH$_2$ Seq. ID No: 9 | ¹H NMR (DMSO-d$_6$, 300 MHz): δ = 0.87 (t, J = 6.6 Hz, 6H), 1.14 (s, 9H), 1.40-2.07 (m, 16H), 2.48-2.71 (m, 8H), 3.02-3.08 (m, 5H), 3.39-3.60 (m, 3H), 3.81 (d, J = 5.7 Hz, 2H), 4.14-4.25 (m, 2H), 4.35-4.44 (m, 1H), 6.44-6.75 (m, 2H), 7.08-7.36 (m, 8H), 7.97-8.09 (m, 3H), 8.34-8.38 (m, 1H). ¹³C NMR (DMSO-d$_6$, 75 MHz): δ = 12.6, 18.0, 18.3, 19.3, 19.5, 27.4, 28.7, 31.2, 42.8, 52.6, 53.7, 56.4, 57.5, 62.2, 73.5, 86.7, 116.6, 124.7, 126.5, 128.5, 129.7, 131.8, 137.6, 139.0, 156.4, 157.8, 169.3, 170.0, 171.7, 173.6, 174.5. |
| H-Met-Glu(OtBu)-Glu(OtBu)-Glu(OtBu)-Ala-NH$_2$ Seq. ID No: 10 | ¹H NMR (DMSO-d$_6$, 300 MHz): δ = 1.13 (d, J = 6.9 Hz, 3H), 1.32 (s, 27H), 1.45-1.96 (m, 13H), 2.12-2.19 (m, 6H), 3.15-3.25 (m, 1H), 4.05-4.23 (m, 4H), 6.91 (s, 1H), 7.20 (s, 1H), 7.79 (d, J = 7.2 Hz, 1H), 7.91 (d, J = 7.5 Hz, 1H), 8.02 (d, J = 7.8 Hz, 1H). ¹³C NMR (DMSO-d$_6$, 75 MHz): δ = 15.0, 18.6, 27.5, 28.0, 28.1, 30.2, 31.6, 35.0, 48.4, 51.8, 52.1, 54.2, 80.0, 170.7, 171.3, 171.5, 172.0, 172.1, 174.3, 175.2. |
| H-Ser(tBu)-Lys(Boc)-Gln(Trt)-Met-Glu(OtBu)-NH$_2$ Seq. ID No: 11 | ¹H NMR (DMSO-d$_6$, 300 MHz): δ = 1.18 (s, 9H), 1.30-2.50 (m, 39H), 2.90-2.98 (m, 2H), 3.51-3.71 (m, 2H), 3.97-4.00 (m, 1H), 4.22-4.27 (m, 2H), 4.38-4.42 (m, 2H), 6.79-6.85 (m, 1H), 7.06 (s, 1H), 7.21-7.39 (m, 17H), 7.95-8.26 (m, 6H), 8.54-8.60 (m, 2H). ¹³C NMR (DMSO-d$_6$, 75 MHz): δ = 15.0, 22.9, 27.4, 27.7, 28.1, 28.7, 29.7, 31.7, 32.4, 32.6, 33.0, 52.0, 52.3, 52.8, 52.9, 53.2, 61.0, 74.0, 77.8, 80.1, 126.7, 127.8, 128.9, 145.2, 155.9, 166.6, 171.1, 171.3, 171.4, 171.7, 172.0, 173.2. |
| H-Leu-Phe-Ile-Glu(OtBu)-Trp(Boc)-NH$_2$ Seq. ID No: 12 | ¹H NMR (DMSO-d$_6$, 300 MHz): δ = 0.75-0.85 (m, 12H), 0.99-1.93 (m, 25H), 2.16-2.22 (m, 2H), 2.73-3.12 (m, 4H), 4.14-4.19 (m, 1H), 4.24-4.32 (m, 1H), 4.49-4.63 (m, 2H), 7.15-7.36 (m, 8H), 7.50 (s, 1H), 7.69 (d, J = 7.8 Hz, 1H), 8.00-8.32 (m, 4H). ¹³C NMR (DMSO-d$_6$, 75 MHz): δ = 11.3, 15.6, 22.2, 23.4, 24.1, 24.7, 27.8, 28.1, 31.5, 36.7, 37.8, 43.1, 52.3, 52.7, 53.7, 57.3, 80.0, 83.8, 115.0, 116.9, 119.8, 122.8, 124.1, 124.6, 126.5, 128.3, 129.6, 130.7, 135.0, 137.9, 149.4, 171.1, 171.2, 172.0, 173.0, 173.4. |
| H-Trp(Boc)-Met-Asp($^t$Bu)-Phe-NH$_2$ Seq. ID No: 13 | ¹H NMR (DMSO-d$_6$, 300 MHz): δ = 1.36 (s, 9H), 1.69 (s, 9H), 1.70-3.03 (m, 5H), 2.64-3.22 (m, 5H), 4.08-4.15 (m, 1H), 4.36-4.47 (m, 2H), 4.55-4.63 (m, 1H), 7.14-7.36 (9H), 7.64 (s, 1H), 7.78 (d, J = 7.5 Hz, 1H), 7.93 (d, J = 8.1 Hz, 1H), 8.04-8.11 (m, 5H), 8.40 (d, J = 7.8 Hz, 1H), 8.90 (d, J = 8.1 Hz, 1H). ¹³C NMR (DMSO-d$_6$, 75 MHz): δ = 15.0, 22.9, 27.4, 28.0, 28.1, 29.8, 32.1, 37.5, 37.8, 50.0, 52.4, 52.9, 54.3, 80.7, 83.9, 115.0, 117.1, 119.8, 122.7, 124.3, 124.6, 126.6, 128.4, 129.4, 130.7, 135.0, 138.1, 149.4, 169.8, 169.9, 170.2, 171.2, 171.9, 172.8. |
| H-Glu($^t$Bu)-Glu($^t$Bu)-Glu($^t$Bu)-Ala-Val-NH$_2$ Seq. ID No: 14 | ¹H NMR (DMSO-d$_6$, 300 MHz): δ = 0.85 (t, J = 6.9 Hz, 6H), 1.20 (d, J = 7.2 Hz, 3H), 1.39-1.41 (m, 27H), 1.62-1.99 (m, 7H), 2.20-2.36 (m, 6H), 3.77-3.81 (m, 1H), 4.09-4.14 (m, 1H), 4.24-4.40 (m, 3H), 7.02 (s, 1H), 7.36 (s, 1H), 7.65 (d, J = 9.0 Hz, 1H), 7.87 (s, 2H), 8.10 (d, J = 7.2 Hz, 1H), 8.20 (d, J = 7.5 Hz, 1H), 8.52 (d, J = 7.2 Hz, 1H). |

EXAMPLE 1

Fragment Coupling of Protected Oligopeptide Activated Esters i) with Protected Oligopeptide C-Terminal Amide Nucleophiles ii)

3 μmol of protected oligopeptide activated ester and 4.5 μmol of protected oligopeptide C-terminal amide nucleophile were dissolved in 0.5 mL dichloromethane and 10 mg of crushed molecular sieves were added. Subsequently, 0.5 mL of a stock solution (stored on molecular sieves) containing Alcalase-CLEA-OM (20 mg/mL in dichloromethane) was added. This mixture was shaken at 37° C. with 200 rpm for 24 h and analysed by LC-MS.

EXAMPLE 2

Fragment Coupling of Ac-Asp(OtBu)-Leu-Ser(tBu)-Lys(Boc)-Gln-OCam (Oligopeptide i) with $R_1$ and $R_2$ Hydrogen) H-Met-Glu(OtBu)-Glu(OtBu)-Glu(OtBu)-Val-$NH_2$ (Oligopeptide ii) in Various Solvents 2.2 mmol Ac-Asp(OtBu)-Leu-Ser(tBu)-Lys(Boc)-Gln-OCam (Seq. ID No: 16) and 3.3 mmol H-Met-Glu(OtBu)-Glu(OtBu)-Glu(OtBu)-Val-$NH_2$ (Seq. ID No: 21) were dissolved in 100 μL DMF. Subsequently, 10 mg crushed molecular sieves, 10 mg Alcalase-CLEA-OM and 900 μL of solvent was added. These mixtures were shaken at 37° C. with 200 rpm for 24 h and analysed by HPLC.

TABLE 1

| protected oligopeptide activated ester | protected oligopeptide nucleophile | protected oligopeptide product |
|---|---|---|
| Ac-Asp(OtBu)-Leu-Ser(tBu)-Lys(Boc)-Gln(Trt)-OCam Seq. ID No: 15 | H-Met-Glu(OtBu)-Glu(OtBu)-Glu(OtBu)-Ala-$NH_2$ Seq. ID No: 21 | Ac-Asp(OtBu)-Leu-Ser(tBu)-Lys(Boc)-Gln(Trt)-Met-Glu(OtBu)-Glu(OtBu)-Glu(OtBu)-Ala-$NH_2$ Seq. ID No: 24 |
| Ac-Asp(OtBu)-Leu-Ser(tBu)-Lys(Boc)-Gln-OCam Seq. ID No: 16 | H-Met-Glu(OtBu)-Glu(OtBu)-Glu(OtBu)-Ala-$NH_2$ Seq. ID No: 21 | Ac-Asp(OtBu)-Leu-Ser(tBu)-Lys(Boc)-Gln-Met-Glu(OtBu)-Glu(OtBu)-Glu(OtBu)-Ala-$NH_2$ Seq. ID No: 25 |
| Ac-Thr(tBu)-Ser(tBu)-Asp(OtBu)-Leu-Ser(tBu)-Lys(Boc)-Gln-OCam Seq. ID No: 17 | H-Met-Glu(OtBu)-Glu(OtBu)-Glu(OtBu)-Ala-$NH_2$ Seq. ID No: 21 | Ac-Thr(tBu)-Ser(tBu)-Asp(OtBu)-Leu-Ser(tBu)-Lys(Boc)-Gln-Met-Glu(OtBu)-Glu(OtBu)-Glu(OtBu)-Ala-$NH_2$ Seq. ID No: 26 |
| Ac-Thr(tBu)-Phe-Thr(tBu)-Ser(tBu)-Asp(OtBu)-Leu-Ser(tBu)-Lys(Boc)-Gln-OCam Seq. ID No: 18 | H-Met-Glu(OtBu)-Glu(OtBu)-Glu(OtBu)-Ala-$NH_2$ Seq. ID No: 21 | Ac-Thr(tBu)-Phe-Thr(tBu)-Ser(tBu)-Asp(OtBu)-Leu-Ser(tBu)-Lys(Boc)-Gln-Met-Glu(OtBu)-Glu(OtBu)-Glu(OtBu)-Ala-$NH_2$ Seq. ID No: 27 |
| Ac-Leu-Asp(OtBu)-Gln(Trt)-Ser(tBu)-Gln-OCam Seq. ID No: 19 | H-Phe-Val-Gly-Ser(tBu)-Arg(Pbf)-$NH_2$ Seq. ID No: 22 | Ac-Leu-Asp(OtBu)-Gln(Trt)-Ser(tBu)-Gln-Phe-Val-Gly-Ser(tBu)-Arg(Pbf)-$NH_2$ Seq. ID No: 28 |
| Ac-Thr(tBu)-Phe-Thr(tBu)-Ser(tBu)-Asp(OtBu)-Leu-Ser(tBu)-Lys(Boc)-Gln-OCam Seq. ID No: 20 | H-Ala-Met-Val-Ser(tBu)-Tyr(tBu)-Pro-Arg(Pbf)-Glu(tBu)-Asn(trt)-His(trt)-$NH_2$ Seq. ID No: 23 | Ac-Thr(tBu)-Phe-Thr(tBu)-Ser(tBu)-Asp(OtBu)-Leu-Ser(tBu)-Lys(Boc)-Gln-Ala-Met-Val-Ser(tBu)-Tyr(tBu)-Pro-Arg(Pbf)-Glu(tBu)-Asn(trt)-His(trt)-$NH_2$ Seq. ID No: 29 |
|  | Yield (%) | m/z calcd and found: |
|  | 86 | $C_{93}H_{144}N_{13}O_{23}S^+$: 1843.0, 1842.8 |
|  | 100 | $C_{74}H_{130}N_{13}O_{23}S^+$ 1600.9, 1601.1 |
|  | 98 | $C_{89}H_{158}N_{15}O_{27}S^+$: 1901.1, 1901.4 |
|  | 78 | $C_{106}H_{183}N_{17}O_{30}S^{2+}$: 1103.2, 1103.5 |
|  | 86 | $C_{94}H_{134}N_{16}NaO_{20}S^+$: 1862.0, 1862.3 |
|  | 95[a] | $C_{185}H_{268}N_{28}O_{37}S_2^{2+}$: 1769.0, 1769.5 |

[a]After 7 days of reaction

Table 1 demonstrates that a variety of protected oligopeptide C-terminal esters can be coupled with a variety of protected oligopeptide C-terminal amide nucleophiles giving high yields of the peptide products up to at least 19 amino acids length. Moreover, good yields were obtained without using a large stoichiometric excess of any of the fragments used in the condensation reaction.

| Solvent | Product yield (%) |
|---|---|
| MTBE (containing 10 vol % DMF) | 100 |
| Me-THF (containing 10 vol % DMF) | 96 |
| Dimethoxyethane (containing 10 vol % DMF) | 95 |
| 1,2-dichloroethane (containing 10 vol % DMF) | 96 |
| HFIP[a]/MTBE 1/1 (containing 10 vol % DMF) | 37 |

-continued

| Solvent | Product yield (%) |
|---|---|
| TFE[b]/MTBE 1/1 (containing 10 vol % DMF) | 93 |
| DMF | 65[c] |

[a]1,1,1,3,3,3-hexafluoroisopropanol;
[b]2,2,2-trifluoroethanol;
[c]using 50 mg Alcalase-CLEA-OM.

This table demonstrates that various solvents can be used for the protected oligopeptide fragment coupling reaction.

EXAMPLE 3

Comparison of OCam-Xxx-NH$_2$ Esters (Oligopeptide Esters i) with R$_2$ an Amino Acid Residue with a C-Terminal Carboxyamide Functionality)

Various Cbz-Val-Ala-OCam-Xxx-NH$_2$ esters were compared to Cbz-Val-Ala-OCam in a coupling reaction with H-Phe-NH$_2$. 0.028 mmol CBz-Val-Ala-OCam-Xxx-NH$_2$ or Cbz-Val-Ala-OCam was added to H-Phe-NH$_2$ (1.5 equiv) in 1.5 mL THF (containing 10 vol % DMF) with 5 balls of molecular sieves. The reaction mixtures were stirred at 50° C. for 30 min followed by the addition of 50 mg Alcalase immobilized on decalite. After 1 h of stirring at 50° C., 100 μL aliquots of the reaction mixtures were added to 900 μL DMF and the samples were analyzed by HPLC. Yields were determined from a Cbz-Val-Ala-Phe-NH$_2$ product callibration graph. It should be noted that after 1 h the differences between the various oligopeptide activated esters become well visible. Using prolonged reaction times and/or more enzyme, all reactions could be brought to complete conversion.

| Cbz-Val-Ala-OCam-Xxx-NH$_2$, Xxx = | Cbz-Val-Ala-Phe-NH$_2$, product yield (%) |
|---|---|
| Leu | 64 |
| Asp(OtBu) | 62 |
| Ser(tBu) | 62 |
| Gln(Trt) | 57 |
| Gly | 51 |
| Ala | 51 |
| - - - (normal OCam-ester) (R$_1$ and R$_2$ is H) | 50 |
| Glu(OtBu) | 47 |
| Arg(Pbf) | 46 |
| Phe | 43 |
| Cys(Trt) | 40 |
| Pro | 40 |
| Trp(Boc) | 39 |
| Tyr(tBu) | 38 |
| Thr(tBu) | 36 |
| Ile | 34 |
| Met | 21 |
| Lys(Boc) | 19 |
| Asn(Trt) | 18 |
| His(Trt) | 6 |
| Val | 3 |

This table shows that various C-terminal —OCam-Xxx-NH$_2$ esters can be used for the enzymatic coupling reactions.

EXAMPLE 4

Comparison of OCam-Ester and OCam-Leu-NH$_2$ Ester

3 μmol of protected oligopeptide C-terminal ester and 4.5 μmol of H-Met-Glu(tBu)-Glu(tBu)-Glu(tBu)-Ala-NH$_2$ (Seq. ID No: 21) were dissolved in 0.5 mL dichloromethane and 10 mg of crushed molecular sieves were added. Subsequently, 0.5 mL of a stock solution (stored on molecular sieves) containing Alcalase-CLEA-OM (40 mg/mL in dichloromethane) was added. This mixture was shaken at 37° C. with 200 rpm for 48 h and analysed by LC-MS.

| Protected oligopeptide C-terminal ester | Product yield (%) | m/z calcd and found: |
|---|---|---|
| Ac-Asp(OtBu)-Leu-Ser(tBu)-Lys(Boc)-Gln(Trt)-OCam(R$_1$ and R$_2$ hydrogen) Seq. ID No: 30 | 86 | C$_{93}$H$_{144}$N$_{13}$O$_{23}$S$^+$: 1843.0, 1843.1 |
| Ac-Asp(OtBu)-Leu-Ser(tBu)-Lys(Boc)-Gln(Trt)-OCam-Leu-NH$_2$ (R$_1$ hydrogen and R$_2$ an amino acid residue with a C-terminal carboxyamide functionality) Seq. ID No: 31 | 95 | C$_{93}$H$_{144}$N$_{13}$O$_{23}$S$^+$: 1843.0, 1842.9 |

This outcome demonstrates that the results shown in Example 3 for [2+1] couplings can be translated to peptide fragment couplings and that at least in some cases the use of C-terminal —OCam-Xxx-NH$_2$ esters of protected oligopeptides is advantageous for the coupling rate and yield compared to unsubstituted —OCam esters.

EXAMPLE 5

Comparison of Oligopeptide-OCam-Xxx-NH$_2$ (C-Terminal Carboxamide Functionality) and Oligopeptide-OCam-Xxx-OH Esters (C-Terminal Carboxylic Acid Functionality)

Cbz-Val-Ala-OCam-Leu-NH$_2$ and Cbz-Val-Ala-OCam-Leu-OH, were enzymatically condensed with H-Phe-NH$_2$ as described in example 3. Cbz-Val-Gln(Trt)-OCam-Gly-NH$_2$ and Cbz-Val-Gln(Trt)-OCam-Gly-OH were enzymatically condensed with H-Phe-NH$_2$ as described in example 3 but five times the amount of enzyme was used. Piperidine (1 equiv.) was used to neutralize the carboxylic acid moieties prior to the enzymatic coupling.

| Oligopeptide C-terminal ester | Product yield (%) |
|---|---|
| Cbz-Val-Ala-OCam-Leu-NH$_2$ | 56 |
| Cbz-Val-Ala-OCam-Leu-OH | 51 |
| Cbz-Val-Gln(Trt)-OCam-Gly-NH$_2$ | 90 |
| Cbz-Val-Gln(Trt)-OCam-Gly-OH | 86 |

This outcome shows that C-terminal —OCam-Xxx-NH$_2$ esters as well as —OCam-Xxx-OH esters can be used for the enzymatic coupling reaction and display a comparable reaction rate in at least some cases.

EXAMPLE 6

Use of Various Enzymes and Immobilisation Forms 2.2 mmol Ac-Asp(OtBu)-Leu-Ser(tBu)-Lys(Boc)-Gln-OCam and 3.3 mmol H-Met-Glu(OtBu)-Glu(OtBu)-Glu(OtBu)-Val-NH$_2$ were dissolved in 100 μL DMF. Subsequently, 10 mg crushed molecular sieves, 10 mg enzyme and 900 μL MTBE were added. These mixtures were shaken at 37° C. with 200 rpm for 24 h and analysed by HPLC. The following enzymes gave excellent product yields (>80%):

Alcalase-CLEA-OM, Alcalase-imibond, Alcalase-epobond, Alcalase-immozyme, Liquid Alcalase, Subtilisine A, Proteinase K.

2.2 mmol Cbz-Phe-OCam and 3.3 mmol H-Phe-NH$_2$ were dissolved in 100 µL DMF. Subsequently, 10 mg crushed molecular sieves, 10 mg enzyme and 900 µL MTBE were added. These mixtures were shaken at 37° C. with 200 rpm for 24 h and analysed by HPLC. The following enzymes gave excellent product yields (>80%): Savinase, Esperase, Everlase, Protease from *Bacillus* sp. (three available variants), Protease from *Bacillus licheniformis*.

EXAMPLE 7

Fragment Coupling of Protected Oligopeptide Activated Cam-Esters i) with H-Leu-Phe-NH$_2$ 3 µmol of protected oligopeptide acyl donor was dissolved in 0.5 mL dichloromethane and 10 mg of crushed molecular sieves were added. Subsequently, 0.5 mL of a stock solution (stored on molecular sieves) containing 12 µmol/mL H-Leu-Phe-NH$_2$ and 20 mg/mL Alcalase-CLEA-OM in dichloromethane was added. This mixture was shaken at 37° C. with 200 rpm for 24 h and analysed by LC-MS. It should be noted that after 24 h the differences between the various Cam-esters become well visible. Using prolonged reaction times and/or more enzyme, all reactions could be brought to complete conversion.

As can be observed in entries 1-4, various side chain protecting groups can be used for the C-terminal Gln residue of the oligopeptide C-terminal ester, but it is advantageous if this C-terminal Gln residue has an unprotected side chain functionality. Entries 5-13 confirm that protected oligopeptide C-terminal esters with a variety of amino acid sequences and side chain protective groups can be used in the enzymatic coupling reaction.

EXAMPLE 8

Coupling of Protected Oligopeptide C-Terminal Amide Nucleophiles ii) with Cbz-Phe-OCam 3 µmol of protected oligopeptide C-terminal amide nucleophile was dissolved in 0.5 mL dichloromethane and 10 mg of crushed molecular sieves were added. Subsequently, 0.5 mL of a stock solution (stored on molecular sieves) containing 12 µmol/mL Cbz-Phe-OCam and 20 mg/mL Alcalase-CLEA-OM in dichloromethane was added. This mixture was shaken at 37° C. with 200 rpm for 24 h and analysed by LC-MS. It should be noted that after 24 h the differences between the various protected oligopeptide C-terminal amide nucleophiles become well visible. Using prolonged reaction times and/or more enzyme, all reactions could be brought to complete conversion.

| Entry | Protected oligopeptide activated ester | Product yield (%) | m/z calcd and found: |
|---|---|---|---|
| 1 | Ac-Asp(OtBu)-Leu-Ser(tBu)-Lys(Boc)-Gln(Xan)-OCam Seq. ID No: 32 | 13 | $C_{67}H_{98}N_{10}NaO_{15}^+$: 1305.7; 1305.5 |
| 2 | Ac-Asp(OtBu)-Leu-Ser(tBu)-Lys(Boc)-Gln(Trt)-OCam Seq. ID No: 33 | 18 | $C_{73}H_{104}N_{10}NaO_{14}^+$: 1367.8; 1367.6 |
| 3 | Ac-Asp(OtBu)-Leu-Ser(tBu)-Lys(Boc)-Gln(Tmob)-OCam Seq. ID No: 34 | 37 | $C_{64}H_{102}N_{10}NaO_{17}^+$: 1305.7; 1305.4 |
| 4 | Ac-Asp(OtBu)-Leu-Ser(tBu)-Lys(Boc)-Gln-OCam Seq. ID No: 35 | 92 | $C_{54}H_{90}N_{10}NaO_{14}^+$: 1125.7; 1125.5 |
| 5 | Ac-Thr(tBu)-Ser(tBu)-Asp(OtBu)-Leu-Ser(tBu)-Lys(Boc)-Gln-OCam Seq. ID No: 36 | 91 | $C_{69}H_{118}N_{12}NaO_{18}^+$: 1425.9, 1425.6 |
| 6 | Ac-Thr(tBu)-Phe-Thr(tBu)-Ser(tBu)-Asp(OtBu)-Leu-Ser(tBu)-Lys(Boc)-Gln-OCam Seq. ID No: 37 | 97 | $C_{86}H_{142}N_{14}NaO_{21}^+$: 1730.0, 1730.8 |
| 7 | Ac-Glu(tBu)-Gly-Thr(tBu)-Phe-Thr(tBu)-Ser(tBu)-Asp(OtBu)-Leu-Ser(tBu)-Lys(Boc)-Gln-OCam Seq. ID No: 38 | 53 | $C_{97}H_{161}N_{16}O_{25}^+$: 1950.2, 1950.7 |
| 8 | Ac-Phe-Ile-Glu(OtBu)-Trp(Boc)-Leu-OCam Seq. ID No: 39 | 93 | $C_{63}H_{89}N_9NaO_{12}^+$: 1186.7, 1186.5 |
| 9 | Ac-Leu-Ser(tBu)-Lys(Boc)-Gln(Trt)-Met-OCam Seq. ID No: 40 | 15 | $C_{70}H_{100}N_{10}NaO_{12}S^+$: 1327.7, 1327.5 |
| 10 | Ac-Glu(OtBu)-Glu(OtBu)-Ala-Val-Arg(Pbf)-OCam Seq. ID No: 41 | 96 | $C_{62}H_{98}N_{11}O_{15}S^+$: 1268.7, 1268.5 |
| 11 | Ac-Phe-Thr(tBu)-Ser(tBu)-Asp(OtBu)-Leu-OCam Seq. ID No: 42 | 24 | $C_{55}H_{86}N_8NaO_{12}^+$: 1073.6, 1073.5 |
| 12 | Ac-Leu-Asp(OtBu)-Gln(Trt)-Ser(tBu)-Gln-OCam Seq. ID No: 43 | 68 | $C_{67}H_{92}N_{10}NaO_{13}^+$ 1267.7, 1267.5 |
| 13 | Ac-His(Trt)-Lys(Boc)-Thr(tBu)-Asp(OtBu)-Ser-OCam Seq. ID No: 44 | 73 | $C_{53}H_{85}N_{11}NaO_{14}^+$: 1122.6, 1122.6 (fragment without Trt) |

| Entry | Protected oligopeptide nucleophile | Product yield (%) | m/z Calcd and found: |
|---|---|---|---|
| 1 | H-Phe-Val-Gly-Ser(tBu)-Arg(Pbf)-NH$_2$<br>Seq. ID No: 45 | 45 | $C_{59}H_{81}N_{10}O_{12}S^+$<br>1153.6, 1153.3 |
| 2 | H-Met-Glu(OtBu)-Glu(OtBu)-Glu(OtBu)-Ala-NH$_2$<br>Seq. ID No: 21 | 58 | $C_{52}H_{77}N_7NaO_{14}S^+$:<br>1078.5, 1078.3 |
| 3 | H-Ser(tBu)-Lys(Boc)-Gln(Trt)-Met-Glu(OtBu)-NH$_2$<br>Seq. ID No: 46 | 23 | $C_{73}H_{97}N_9NaO_{14}S^+$:<br>1378.7, 1378.5 |
| 4 | H-Leu-Phe-Ile-Glu(OtBu)-Trp(Boc)-NH$_2$<br>Seq. ID No: 47 | 23 | $C_{63}H_{82}N_8NaO_{12}^+$:<br>1165.6, 1165.4 |
| 5 | H-Lys(Boc)-Asn(Trt)-Gly-Gly-Pro-NH$_2$<br>Seq. ID No: 48 | 29 | $C_{60}H_{71}N_9NaO_{11}^+$<br>1116.5, 1116.5 |
| 6 | H-Trp(Boc)-Met-Asp($^t$Bu)-Phe-NH$_2$<br>Seq. ID No: 49 | 100 | $C_{55}H_{67}N_7NaO_{11}S^+$:<br>1056.5, 1156.3 |
| 7 | H-Glu($^t$Bu)-Glu($^t$Bu)-Glu($^t$Bu)-Ala-Val-NH$_2$<br>Seq. ID No: 50 | 19 | $C_{52}H_{77}N_7NaO_{14}^+$:<br>1046.5, 1146.4 |
| 8 | H-Ser(tBu)-Leu-Leu-NH$_2$ | 59 | $C_{36}H_{53}N_5NaO_7^+$:<br>690.4, 690.4 |
| 9 | H-Ala-Met-Val-Ser($^t$Bu)-Tyr($^t$Bu)-Pro-Arg(Pbf)-Glu($^t$Bu)-Asn(trt)-His(trt)-NH$_2$<br>Seq. ID No: 51 | 53 | $C_{130}H_{160}N_{18}O_{21}S_2^{2+}$:<br>1186.6, 1186.2 |

Entries 1-9 confirm that protected oligopeptide C-terminal amide nucleophiles with a variety of amino acid sequences and side-chain protective groups can be used in the enzymatic coupling reaction.

EXAMPLE 9

Influence of Water Content on Synthesis/Hydrolysis Ratio 2.2 µmol Cbz-Phe-OCam and 4.4 µmol H-Phe-NH$_2$ were dissolved in 1 mL dichloromethane and 5 mg of Alcalase-CLEA-OM was added (six of these equal mixtures were prepared). To these mixtures were added 0, 0.1, 0.5, 1.0, 2.0 and 3.0 µL of H$_2$O (corresponding to ≈0, 0.01, 0.05, 0.1, 0.2 and 0.3 vol % water in the reaction mixtures). All six mixtures were shaken at 37° C. with 200 rpm for 2 h and analysed by HPLC.

The S/H ratio is defined as the amount (mmol) of formed dipeptide product Cbz-Phe-Phe-NH$_2$ divided by the amount (mmol) of formed hydrolysis product Cbz-Phe (mmol). As can be seen from enclosed FIG. 1, a low water concentration is essential to avoid hydrolysis of the Cam-ester.

EXAMPLE 10

Enzyme Reactivation by Rehydration

Deactivation 5 mg of Alcalase-CLEA-OM and 25 mg 3 Å molecular sieves were shaken at 37° C. in 1 mL DMF and separately in 1 mL dichloromethane and separately in 1 mL DMF/MTBE (1/9, v/v). For all three solvents three of these equal mixtures were prepared. For all three solvents, the three mixtures were filtrated after 1, 24 and 48 h, respectively, and in each case 1 mL of DMF/THF (1/9, v/v) containing 5 mg Cbz-Phe-OCam and 1.5 equiv. H-Phe-NH$_2$ was added and the reaction mixtures were shaken at 37° C. For comparison, 1 mL of DMF/THF (1/9, v/v) containing 5 mg Cbz-Phe-OCam and 1.5 equiv. H-Phe-NH$_2$ was shaken at 37° C. with 5 mg of Alcalase-CLEA-OM and 25 mg 3 Å molecular sieves that had not been previously shaken in organic solvent. Samples were taken after 1 h and the conversions to Cbz-Phe-Phe-NH$_2$ were determined by HPLC. The relative activities were calculated by dividing the amount of Cbz-Phe-Phe-NH$_2$ (mmol) obtained with Alcalase-CLEA-OM that had been treated with organic solvent by the amount of Cbz-Phe-Phe-NH$_2$ (mmol) obtained with untreated Alcalase-CLEA-OM×100%.

Figure 2:
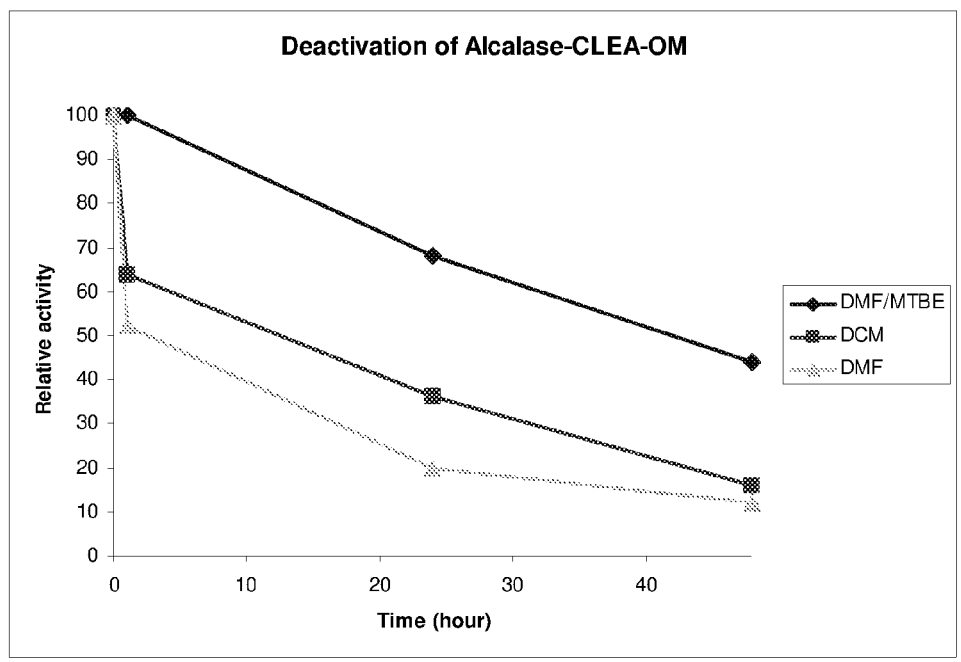
FIG. 2 illustrates deactivation of Alcalase-CLEA-OM in three different organic solvent(s) (mixtures) containing 3 Å molecular sieves.

As can be seen in enclosed FIG. 2, Alcalase-CLEA-OM is slowly deactivated in dry organic solvents containing 3 Å molecular sieves.

Reactivation 5 mg of Alcalase-CLEA-OM and 25 mg 3 Å molecular sieves were shaken at 37° C. in 1 mL DMF and separately in 1 mL dichloromethane and separately in 1 mL DMF/MTBE (1/9, v/v). For all three solvents three of these equal mixtures were prepared. For all three solvents, the three mixtures were filtrated after 1, 24 and 48 h, respectively, and in each case 1 mL of (1/1, v/v) DMF/phosphate buffer (100 mM, pH=7.5) containing 5 mg of Cbz-Val-Phe-OMe was added and the reaction mixtures were shaken at 37° C. For comparison, 1 mL of (1/1, v/v) DMF/phosphate buffer (100 mM, pH=7.5) containing 5 mg of Cbz-Val-Phe-OMe was shaken at 37° C. with 5 mg of Alcalase-CLEA-OM and 25 mg 3 Å molecular sieves that had not been previously shaken in organic solvent. Samples were taken after 1 h and the conversions to Cbz-Val-Phe-OH were determined by HPLC. The relative activities were calculated by dividing the amount of Cbz-Val-Phe-OH (mmol) obtained by the hydrolysis with Alcalase-CLEA-OM that had been treated with organic solvent by the amount of Cbz-Val-Phe-OH (mmol) obtained by the hydrolysis with untreated Alcalase-CLEA-OM×100%.

Figure 3:
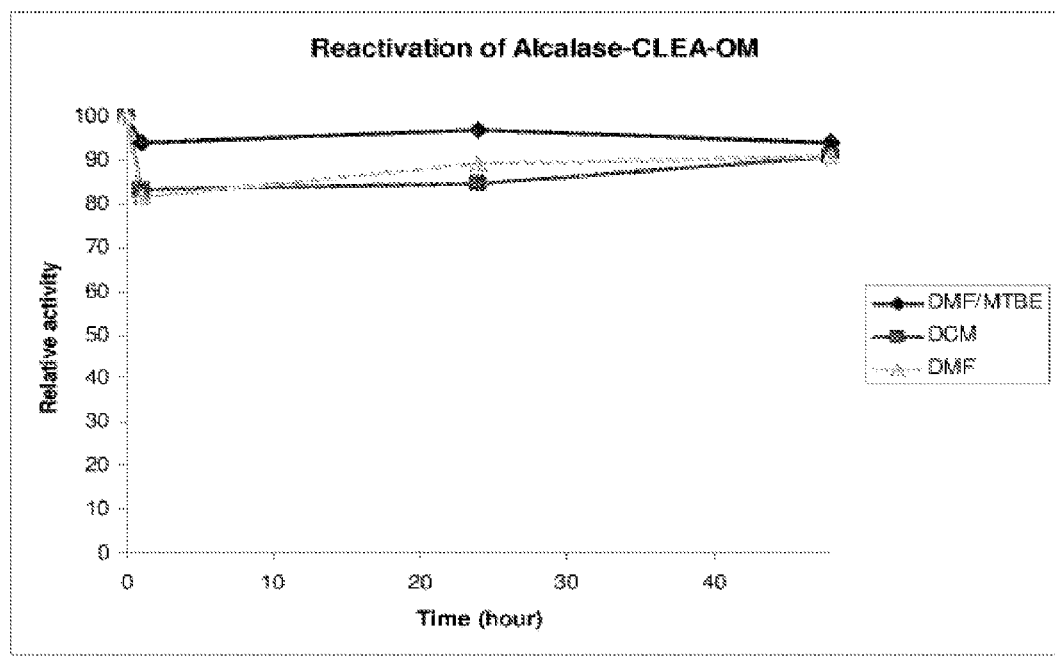
FIG. 3 illustrates reactivation of Alcalase-CLEA-OM in aqueous buffer solution.

As can be seen in enclosed FIG. 3, Alcalase-CLEA-OM that had been deactivated in dry organic solvents containing 3 Å molecular sieves, can be reactivated in aqueous buffer solution.

EXAMPLE 11

Enzyme Deactivation with Various Amounts of Molecular Sieves and Reactivation in Aqueous Buffer Solution Deactivation To four identical mixtures of 10 mg Alcalase-CLEA-OM in 0.5 mL dichloromethane were added, respectively, 10, 20, 30 and 50 mg molecular sieves (3 Å). The mixtures were shaken for 20 h at 37° C. with 200 rpm. Subsequently, 0.5 mL dichloromethane containing 0.2 mM Cbz-Phe-OCam and 0.3 mM H-Phe-NH$_2$ was added and the reaction mixtures were shaken at 37° C. with 200 rpm. Samples were taken after 1 h and the conversions to Cbz-Phe-Phe-NH$_2$ were determined by HPLC. The relative activities were calculated by dividing the amount of Cbz-Phe-Phe-NH$_2$ (mmol) obtained by the enzymatic coupling reaction by the amount of Cbz-Phe-Phe-NH$_2$ (mmol) obtained by the enzymatic coupling reaction with the highest conversion (i.e., in the case of 10 mg molecular sieves)×100%.

Synthesis of Cbz-Phe-Phe-NH$_2$ using Alcalase-CLEA-OM which had been deactivated with various amounts of molecular sieves.

| Alcalase-CLEA-OM treated with | Relative activity (%) |
| --- | --- |
| 10 mg molecular sieves | 100 |
| 20 mg molecular sieves | 82 |
| 30 mg molecular sieves | 69 |
| 50 mg molecular sieves | 58 |

As can be seen in the table above, too dry conditions due to the use of larger amounts of molecular sieves can lead to a higher enzyme deactivation.

Reactivation

Of the four reaction mixtures above the dichloromethane was evaporated using a nitrogen flow. Subsequently, 1 mL 100 mM phosphate buffer (pH 8) containing 5 mg Cbz-Asn-OMe was added and the reaction mixtures were shaken at 37° C. with 200 rpm. Samples were taken after 1 h and the conversions to Cbz-Asn-OH were determined using HPLC. The relative activities were calculated by dividing the amount of Cbz-Asn-OH (mmol) obtained by the enzymatic hydrolysis by the amount of Cbz-Asn-OH (mmol) obtained by the enzymatic hydrolysis with the highest conversion (i.e., in the case of 50 mg molecular sieves)×100%.

Hydrolysis of Cbz-Asn-OMe using Alcalase-CLEA-OM which had been deactivated with various amounts of molecular sieves.

| Reaction mixture containing | Relative activity (%) |
| --- | --- |
| 10 mg molecular sieves | 87 |
| 20 mg molecular sieves | 93 |
| 30 mg molecular sieves | 97 |
| 50 mg molecular sieves | 100 |

As can be seen in the table above, the hydrolytic Alcalase-CLEA-OM activities are comparable and independent of their previous degree of deactivation, showing that the enzymatic activity can be recovered in aqueous solution.

FEATURES USED IN SEQUENCE LISTING

Ac=acetyl
Boc=tert.-butyloxycarbonyl
NH2=amine
OCam=carboxamidomethyl ester
OtBu=tert.butyl ester
Pbf=2,2,4,6,7-pentamethyldihydrobenzo-furan-5-sulfonyl
tBu=tert.butyl
Tmob=2,4,6-trimethoxybenzyl
Trt=trityl
Xan=xanthenyl

What is claimed is:

1. A method for the enzymatic synthesis of an oligopeptide, comprising:
    (i) obtaining an oligopeptide ester by solid phase using a linker, said oligopeptide ester comprising four or more amino acid residues, wherein each of said four or more amino acid residues comprise at least two amino acid residues, each of these two amino acid residues having side-chain functionality that is protected with a protecting group, and an activated C-terminal ester represented by the formula C(=O)—O—CX$_2$—C(=O)N—R$_1$R$_2$;
    wherein each X independently represents a hydrogen atom, an alkyl group or an aryl group;
    wherein R1 represents a hydrogen atom and
    wherein R2 represents an amino acid residue or peptide residue with a C-terminal carboxyamide or carboxylic acid functionality,
    (ii) coupling said oligopeptide ester with an oligopeptide nucleophile, said oligopeptide nucleophile comprising four or more amino acid residues and an N-terminal amine group, wherein each of said four or more amino acid residues comprise at least two amino acid residues, each of these two amino acid residues having side-chain functionality, that is protected with a protecting group;
    wherein said coupling is carried out in an organic solvent or an organic solvent mixture comprising 0.1 vol % or less water relative to the total amount of liquids in which the coupling reaction predominantly takes place,
    wherein said coupling is carried out in the presence of a subtilisin, and
    wherein water that is released by said subtilisin during the coupling reaction is removed.

2. The method according to claim 1, wherein the linker is a Sieber or Ramage linker.

3. The method according to claim 1, wherein at least 50% of all side-chain functionalities are protected.

4. The method according to claim 1, wherein each X represents a hydrogen atom.

5. The method according to claim 1, wherein all side-chain functionalities of the oligopeptide ester and the oligopeptide nucleophile are protected but for the side-chain functionality of the C-terminal amino acid residue of the oligopeptide ester.

6. The method according to claim 1, wherein the subtilisin is a mutant of a wild type subtilisin.

7. The method according to claim 1, wherein the subtilisin is used in an immobilised form.

8. The method according to claim 1, wherein the subtilisin is immobilised in the form of a cross-linked enzyme aggregate (CLEA).

9. The method according to claim 1, wherein the organic solvent or organic solvent mixture comprises MTBE, THF, Me-THF, 1,2-dimethoxyethane, dichloromethane, 1,2-dichloroethane, TFE, DMF, NMP, DMA or DMSO.

10. The method according to claim 9, wherein the organic solvent or organic solvent mixture comprises MTBE, a mixture of MTBE with DMF or NMP or DMA or DMSO, dichloromethane or a mixture of dichloromethane with DMF or NMP or DMA or DMSO.

11. The method according to claim 1, wherein the organic solvent or the organic solvent mixture has a water content of 0.05 vol % or less.

12. The method according to claim 1, wherein water that is released by the enzyme is removed continuously.

13. The method according to claim 1, wherein the water that is released by the enzyme is removed using molecular sieves.

14. The method according to claim 1, wherein the coupling reaction is performed in the absence of a salt.

15. The method according to claim 1, wherein the oligopeptide ester comprises N-terminal protection.

16. The method according to claim 1, wherein the oligopeptide nucleophile comprises C-terminal protection.

17. A method for the enzymatic synthesis of an oligopeptide, comprising:
(i) obtaining an oligopeptide ester by solid phase using a linker, said oligopeptide ester comprising four or more amino acid residues, wherein each of said four or more amino acid residues comprise at least two amino acid residues, each of these two amino acid residues having side-chain functionality that is protected with a protecting group, and an activated C-terminal ester represented by the formula $C(=O)-O-CX_2-C(=O)N-R_1R_2$;
wherein each X independently represents a hydrogen atom, an alkyl group or an aryl group;
wherein $R_1$ represents a hydrogen atom, an alkyl group or an aryl group and
wherein $R_2$ represents an amino acid residue or peptide residue with a C-terminal carboxyamide or carboxylic acid functionality, protected on the side-chain functionality of the amino acid residue or on one or more of the side-chain functionalities of the peptide residue,
(ii) coupling said oligopeptide ester with an oligopeptide nucleophile, said oligopeptide nucleophile comprising four or more amino acid residues and an N-terminal amine group, wherein each of said four or more amino acid residues comprise at least two amino acid residues, each of these two amino acid residues having side-chain functionality, that is protected with a protecting group;
wherein said coupling is carried out in an organic solvent or an organic solvent mixture comprising 0.1 vol % or less water relative to the total amount of liquids in which the coupling reaction predominantly takes place,
wherein said coupling is carried out in the presence of a subtilisin, and
wherein water that is released by said subtilisin during the coupling reaction is removed.

* * * * *